(12) United States Patent
Isaev et al.

(10) Patent No.: US 10,434,145 B2
(45) Date of Patent: Oct. 8, 2019

(54) CODON-OPTIMIZED RECOMBINANT PLASMID, METHOD OF STIMULATING PERIPHERAL NERVE REGENERATION, AND METHOD OF TREATING NERVE DAMAGE IN HUMANS

(71) Applicant: "NEXTGEN" COMPANY LIMITED, Moscow (RU)

(72) Inventors: Artur Aleksandrovich Isaev, Moscow (RU); Albert Anatolyevich Rizvanov, Kazan (RU); Ruslan Faridovich Masgutov, Kazan (RU); Aleksei Andreevich Bogov, Kazan (RU); Ilnur Ildusovich Salafutdinov, Kazan (RU); Roman Vadimovich Deev, St. Petersburg (RU); Ilya Yadigerovich Bozo, Kuvshinovo (RU); Igor Leonidovich Plaksa, Pos. Pervamayskoye (RU); Andrei Alekseevich Bogov, Kazan (RU); Valeriya Vladimirovna Solovyeva, Kazan (RU)

(73) Assignee: "NEXTGEN" COMPANY LIMITED, Moscow (RU)

( * ) Notice: Subject to any disclaimer, the term of this patent is extended or adjusted under 35 U.S.C. 154(b) by 0 days.

(21) Appl. No.: 15/652,792

(22) Filed: Jul. 18, 2017

(65) Prior Publication Data

US 2017/0319658 A1 Nov. 9, 2017

Related U.S. Application Data

(63) Continuation-in-part of application No. 15/460,668, filed on Mar. 16, 2017, which is a continuation of application No. PCT/RU2015/000545, filed on Aug. 27, 2015.

(30) Foreign Application Priority Data

Sep. 16, 2014 (RU) .................. 2014137218

(51) Int. Cl.
| | | |
|---|---|---|
| A61K 31/70 | (2006.01) | |
| C12N 15/63 | (2006.01) | |
| C07H 21/04 | (2006.01) | |
| A61K 38/18 | (2006.01) | |
| C07K 14/475 | (2006.01) | |
| C07K 14/50 | (2006.01) | |
| C12N 15/85 | (2006.01) | |
| C12N 15/79 | (2006.01) | |
| A61K 48/00 | (2006.01) | |

(52) U.S. Cl.
CPC ...... *A61K 38/1866* (2013.01); *A61K 38/1825* (2013.01); *C07K 14/475* (2013.01); *C07K 14/503* (2013.01); *C12N 15/63* (2013.01); *C12N 15/85* (2013.01); *A61K 48/00* (2013.01); *C07H 21/04* (2013.01); *C12N 15/79* (2013.01); *C12N 2800/22* (2013.01); *C12N 2810/00* (2013.01)

(58) Field of Classification Search
CPC .... A61K 48/00; C12N 15/79; C12N 2810/00; C07H 21/04
USPC ............ 514/44 R; 435/320.1; 536/23.5, 23.7
See application file for complete search history.

(56) References Cited

FOREIGN PATENT DOCUMENTS

| EP | 1 732 614 | 12/2008 |
|---|---|---|
| RU | 2 459 630 | 8/2012 |
| RU | 2 517 117 | 5/2014 |

OTHER PUBLICATIONS

Kotterman et al., 2014, Nature Reviews, vol. 15, p. 445-451.*
Kaur et al., 2009, Current Gene Therapy, vol. 9. p. 434-458.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Mayo clinic, Departments and Divisions: Neurology Research, Peripheral nerve disorders, p. 1-4, https://www.mayo.edu/research/departments-divisions/department-neurology/programs/peripheral-nerve-disorders?_ga=2.108912770.1646718473.1542749852-179240118.1528387272, 2018.*
Beazley-Long et al, "VEGF-A165b Is an endogenous neuroprotective splice Isoform of Vascular Endothelial Growth Factor A in Vivo and in Vitro", Journal of Pathology, 2013, vol. 183, No. 3, pp. 918-929.

(Continued)

*Primary Examiner* — Shin Lin Chen
(74) *Attorney, Agent, or Firm* — Oblon, McClelland, Maier & Neustadt, L.L.P.

(57) ABSTRACT

Provided is a method for treating a peripheral nervous system damage or injury, or for regenerating peripheral nervous system tissue that involves administering to a subject in need thereof a vector that comprises polynucleotide sequences that encode a modified vascular endothelia growth factor (VEGF) and a fibroblast growth factor (FGF2) and further a polynucleotide that encodes resistance to kanamycin. A gene-therapeutic structure encoding modified vascular endothelial growth factors (VEGF) and (FGF-2) is also provided. The gene-therapeutic structure can be administered directly to a damaged nerve and paraneural tissues both in intraoperative and post-operative period to stimulate peripheral nerve regeneration. The structure and method significantly advance existing methods for reconstructive treatment for damaged peripheral nerves.

9 Claims, 15 Drawing Sheets
(15 of 15 Drawing Sheet(s) Filed in Color)
Specification includes a Sequence Listing.

(56) References Cited

OTHER PUBLICATIONS

Deitch et al, "Experience with 112 Shotgun Wounds of the Extremities", Journal of Trauma, 1984, vol. 24, No. 7, pp. 600-603.
Forstreuter et al, "Vascular endothelial growth factor induces chemotaxis and proliferation of microglial cells", J. of Neuroimmunology, 2002, vol. 132, pp. 93-98.
Fu et al, "Favorable Effect of Local VEGF Gene Injection on Axonal Regeneration in the Rat Sciatic Nerve", Journal of Huazhong University of Science and Technology, 2007, vol. 27, No. 2, pp. 186-189.
Furusho, et al, "Disruption of Fibroblast Growth Factor Receptor Signaling in Non-Myelinating Schwann Cells Causes Sensory Axonal Neuropathy and Impairment of Thermal Pain Sensitivity", J. Neurosci, 2009, vol. 29, No. 6 (13 pages).
Grothe et al, "Physiological function and putative therapeutic impact of the FGF-2 system in peripheral nerve regeneration—Lessons from in vovo studies in mice and rats", Brain Research Reviews, 2006, vol. 51, pp. 293-299.
Guzen et al, "Sciatic nerve grafting and inoculation of FGF-2 promotes improvement of motor behavior and fiber regrowth in rats with spinal cord transection", Restorative Neurology and Neuroscience, 2012, vol. 30, pp. 265-275.
Haninec et al, "Enhancement of musculocutaneous nerve reinnervation after vascular endothelial growth factor (VEGF) gene therapy", BMC Neuroscience 2012, vol. 13, No. 57 (11 pages).
Hsieh, et al, "The effect of vascular endothelial growth factor and brain-derived neurotrophic factor on cavernosal nerve regeneration in a nerve-crush rat model", BJU International, 2003, vol. 92, pp. 470-475.
Hudson et al, "Timing of peripheral nerve repair: important local neuropath", Clinical Neurosurgery, 1977, vol. 24, pp. 391-405.
Islamov et al, "Induction of VEGF and its Flt-1 receptor after sciatic nerve crush injury", NeuroReport, 2004, vol. 15, No. 13, pp. 2117-2121.
Karagoz et al, "Vascular Endothelial growth factor-loaded poly(lactic-co-glycolic acid) microspheres-induced lateral axonal sprouting into the vein graft . . . ", Microsurgery 2012, vol. 32, No. 8, pp. 635-641.
Masgutov et al, "Stimulation of rat's sciatic nerve post-traumatic regeneration using plasmids expressing vascular Endothelial Growth factor and basic fibroblast growth factor", Cellular Transplantation and Tissue Engineering 2011, vol. 6, No. 3, pp. 67-70—English abstract.
Noble et al, "Analysis of Upper and Lower Extremity Peripheral nerve Injuries in a Population of Patients with Multiple Injuries", Journal of Trauma, 1998, vol. 45, pp. 116-122.
Pereira Lopes, "Double Gene Therapy with Granulocyte colony-stimulating factor and vascular endothelial growth factor acts synergistically to improve nerve regeneration and functional outcome after sciatic nerve injury in mice", Neuroscience, 2013 vol. 230, pp. 184-197.
Riberio-Resende et al, "Bone marrow-derived fibroblast growth factor-2 induces glial cell proliferation in the regenerating peripheral nervous system", Molecular Neurodegeneration, 2012, vol. 7, No. 34 (17 pp.).
Rovak et al, "Effects of Vascular Endothelial Growth Factor on Nerve Regeneration in Acellular Nerve Grafts", Journal of Reconstructive Microsurgery, 2004, vol. 20, No. 1, pp. 53-58.
Silverman et al, "Vascular, Glial and Neuronal Effects of Vascular endothelial Growth Factor in Mesencephalic Explant Cultures", Neuroscience, 1999, vol. 90, No. 4, pp. 1529-1541.
Sondell et al, "Vascular Endothelial Growth Factor has Neurotrophic Activity and Stimulates Axonal Outgrowth, Enhancing Cell survival and Schwann Cell Proliferation in the Peripheral nervous System", The Journal of neuroscience, 1999, vol. 19, No. 14, pp. 5731-5740.
Sondell et al, "Vascular endothelial growth factor stimulates Schwann cell invasion and neovascularization of acellular nerve grafts", Brain Research, 1999, vol. 846, pp. 219-228.
Terenghi , "Peripherial nerve regeneration and neurotrophic factors", J. Anat., 1999, vol. 194, pp. 1-14.
Zeng et al, "Ionically cross-linked chitosan microspheres for controlled release of bioactive nerve growth factor", Int. J. of Pharmaceutics, 2011, vol. 421, pp. 283-290.
Zhu et al, "Vascular endothelial growth factor promotes proliferation of cortical neuron precursors by regulating E2F expression", The FASEB Journal, 2003, vol. 17, pp. 186-193.
Zor et al, "Effect of VEGF Gene Therapy and Hyaluronic Acid film sheath on Peripheral nerve Regeneration", Microsurgery, 2014, vol. 34, No. 3, pp. 209-216.
Written Opinion of the International Searching Authority dated Dec. 10, 2015, in international application No. PCT/RU2015/000545 (w/English translation).
International Search Report dated Dec. 10, 2015, in International application No. PCT/RU2015/000545 (W/English translation).

* cited by examiner

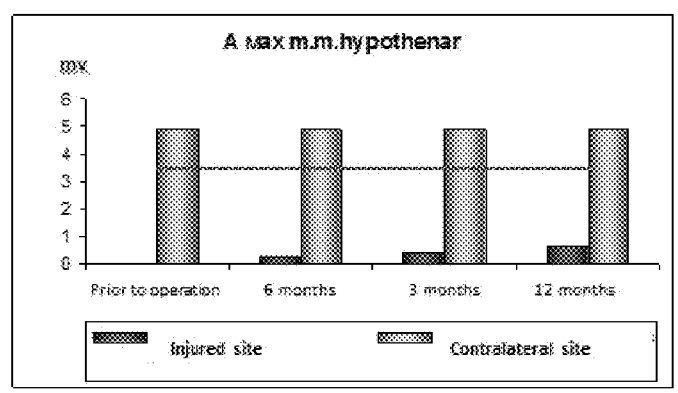
FIG. 15
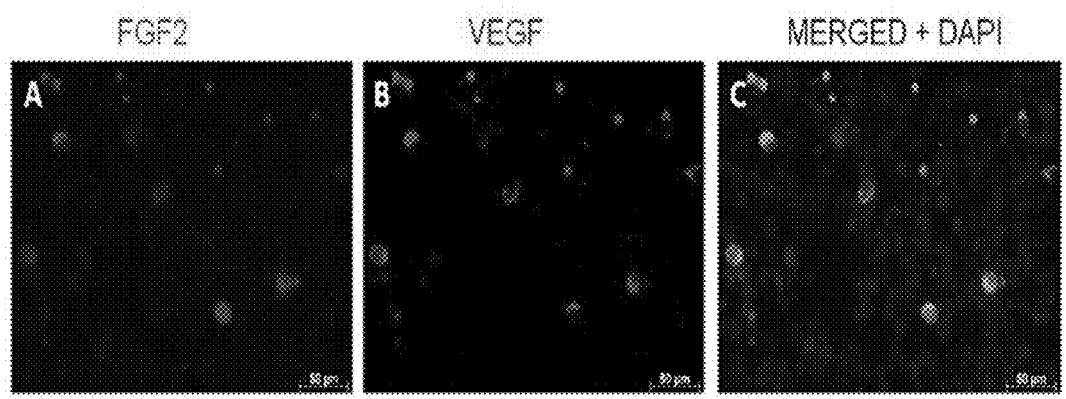
FIG. 16 A, B, C

SEQUENCE LISTING

```
<160> NUMBER OF SEQ ID NOS: 6

<210> SEQ ID NO 1
<211> LENGTH: 5701
<212> TYPE: DNA
<213> ORGANISM: Artificial Sequence
<220> FEATURE:
<223> OTHER INFORMATION: Expression plasmid.  Double-cassette plasmid
      pBud(Kan)-coVEGF165-coFGF2
<220> FEATURE:
<221> NAME/KEY: misc_feature
<222> LOCATION: (695)..(698)
<223> OTHER INFORMATION: Kozak sequence
<220> FEATURE:
<221> NAME/KEY: CDS
<222> LOCATION: (699)..(1166)
<223> OTHER INFORMATION: FGF2 Gene cDNA
<220> FEATURE:
<221> NAME/KEY: misc_feature
<222> LOCATION: (1469)..(2511)
<223> OTHER INFORMATION: Kanamycin resistance gene
<220> FEATURE:
<221> NAME/KEY: misc_feature
<222> LOCATION: (3719)..(3722)
<223> OTHER INFORMATION: Kozak sequence
<220> FEATURE:
<221> NAME/KEY: CDS
<222> LOCATION: (3723)..(4298)
<223> OTHER INFORMATION: VEGF165 Gene cDNA

<400> SEQUENCE: 1
gcgcgcgttg acattgatta ttgactagtt attaatagta atcaattacg gggtcattag     60
```

```
ttcatagccc atatatggag ttccgcgtta cataacttac ggtaaatggc ccgcctggct      120
gaccgcccaa cgaccccgc ccattgacgt caataatgac gtatgttccc atagtaacgc       180
caatagggac tttccattga cgtcaatggg tggactattt acggtaaact gcccacttgg      240
cagtacatca agtgtatcat atgccaagta cgccccctat tgacgtcaat gacggtaaat     300
ggcccgcctg gcattatgcc cagtacatga ccttatggga ctttcctact tggcagtaca    360
tctacgtatt agtcatcgct attaccatgg tgatgcggt ttggcagtac atcaatgggc     420
gtggatagcg gtttgactca cggggatttc caagtctcca ccccattgac gtcaatggga    480
gtttgttttg gcaccaaaat caacgggact ttccaaaatg tcgtaacaac tccgccccat    540
tgacgcaaat gggcggtagg cgtgtacggt gggaggtcta taagcaga gctctctggc      600 taactagaga acccactgct tactggctta tcgaaattaa tacgactcac tatagggaga   660
cccaagctta caagtttgta caaaaaagca ggctcacc atg gca gcc ggg agc atc   716
                                           Met Ala Ala Gly Ser Ile
                                             1               5 acc acg ctg ccc gcc ttg ccc gag gat ggc ggc agc ggc gcc ttc ccg       764
Thr Thr Leu Pro Ala Leu Pro Glu Asp Gly Gly Ser Gly Ala Phe Pro
         10              15              20 ccc ggc cac ttc aag gac ccc aag cgg ctg tac tgc aaa aac ggg ggc       812
Pro Gly His Phe Lys Asp Pro Lys Arg Leu Tyr Cys Lys Asn Gly Gly
     25              30              35 ttc ttc ctg cgc atc cac ccc gac ggc cga gtt gac ggg gtc cgg gag      860
Phe Phe Leu Arg Ile His Pro Asp Gly Arg Val Asp Gly Val Arg Glu
     40              45              50 aag agc gac cct cac atc aag cta caa ctt caa gca gaa gag aga gga     908
Lys Ser Asp Pro His Ile Lys Leu Gln Leu Gln Ala Glu Glu Arg Gly
55              60              65              70 gtt gtg tct atc aaa gga gtg tgt gct aac cgt tac ctg gct atg aag     956
Val Val Ser Ile Lys Gly Val Cys Ala Asn Arg Tyr Leu Ala Met Lys
             75              80              85 gaa gat gga aga tta ctg gct tct aaa tgt gtt acg gat gag tgt ttc    1004
Glu Asp Gly Arg Leu Leu Ala Ser Lys Cys Val Thr Asp Glu Cys Phe
         90              95              100 ttt ttt gaa cga ttg gaa tct aat aac tac aat act tac cgg tca agg    1052
Phe Phe Glu Arg Leu Glu Ser Asn Asn Tyr Asn Thr Tyr Arg Ser Arg
     105             110             115 aaa tac acc agt tgg tat gtg gca ctg aaa cga act ggg cag tat aaa    1100
Lys Tyr Thr Ser Trp Tyr Val Ala Leu Lys Arg Thr Gly Gln Tyr Lys
         120             125             130 ctt gga tcc aaa aca gga cct ggg cag aaa gct ata ctt ttt ctt cca    1148
Leu Gly Ser Lys Thr Gly Pro Gly Gln Lys Ala Ile Leu Phe Leu Pro
135             140             145             150 atg tct gct aag agc tga acccagcttt cttgtacaaa gtggtgtttg            1196
Met Ser Ala Lys Ser
                155 atccccggga attcagacat gataagatac attgatgagt ttggacaaac cacaactaga   1256 atgcagtgaa aaaaatgctt tatttgtgaa atttgtgatg ctattgcttt atttgtaacc   1316 attataagct gcaataaaca agttggggtg gcgaagaac tccagcatga atccccgcg     1376 ctggaggatc atccagccgg cgtcccggaa aacgattccg aagcccaacc tttcatagaa   1436 ggcggcggtg gaatcgaaat ctcgtagcac gtggtctgac gctcagtgga acgacgcgta   1496 actcacgtta agggattttg gtcatgagct tgcgccgtcc cgtcaagtca gcgtaatgct   1556 ctgccagtgt tacaaccaat taaccaattc tgattagaaa aactcatcga gcatcaaatg   1616
```

```
aaactgcaat ttattcatat caggattatc aataccatat ttttgaaaaa gccgtttctg    1676
taatgaagga gaaaactcac cgaggcagtt ccataggatg gcaagatcct ggtatcggtc    1736
tgcgattccg actcgtccaa catcaataca acctattaat ttcccctcgt caaaataag     1796 gttatcaagt gagaaatcac catgagtgac gactgaatcc ggtgagaatg gcaaaagttt    1856
atgcatttct ttccagactt gttcaacagg ccagccatta cgctcgtcat caaaatcact    1916
cgcatcaacc aaaccgttat tcattcgtga ttgcgcctga gcgagacgaa atacgcgatc    1976
gctgttaaaa ggacaattac aaacaggaat cgaatgcaac cggcgcagga acactgccag    2036
cgcatcaaca atattttcac ctgaatcagg atattcttct aatacctgga atgctgtttt    2096
tccggggatc gcagtggtga gtaaccatgc atcatcagga gtacggataa aatgcttgat    2156
ggtcggaaga ggcataaatt ccgtcagcca gtttagtctg accatctcat ctgtaacatc    2216
attggcaacg ctacctttgc catgtttcag aaacaactct ggcgcatcgg gcttcccata    2276
caagcgatag attgtcgcac ctgattgccc gacattatcg cgagcccatt tatacccata    2336
taaatcagca tccatgttgg aatttaatcg cggcctcgac gtttcccgtt gaatatggct    2396
cataacaccc cttgtattac tgtttatgta agcagacagt tttattgttc atgatgatat    2456 tatttatct tgtgcaatgt aacatcagag attttgagac acgggccaga gctgctcgtc    2516
gagctagctt cgtgaggctc cggtgcccgt cagtgggcag agcgcacatc gcccacagtc    2576
cccgagaagt tgggggagg ggtcggcaat tgaaccggtg cctagagaag gtggcgcggg    2636
gtaaactggg aaagtgatgt cgtgtactgg ctccgccttt ttcccgaggg tgggggagaa    2696
ccgtatataa gtgcagtagt cgccgtgaac gttcttttc gcaacgggtt tgccgccaga    2756
acacaggtaa gtgccgtgtg tggttcccgc gggcctggcc tctttacggg ttatggccct    2816
tgcgtgcctt gaattacttc cacctggctc cagtacgtga ttcttgatcc cgagctggag    2876
ccaggggcgg gccttgcgct ttaggagccc cttcgcctcg tgcttgagtt gaggcctggc    2936
ctgggcgctg gggccgccgc gtgcgaatct ggtggcacct tcgcgcctgt ctcgctgctt    2996
tcgataagtc tctagccatt taaaatttt gatgacctgc tgcgacgctt ttttctggc      3056 aagatagtct tgtaaatgcg ggccaggatc tgcacactgg tatttcggtt tttgggcccg    3116
cggccggcga cggggcccgt gcgtcccagc gcacatgttc ggcgaggcgg ggcctgcgag    3176
cgcggccacc gagaatcgga cggggtagt ctcaagctgg ccggcctgct ctggtgcctg     3236
gcctcgcgcc gccgtgtatc gccccgccct gggcggcaag gctggcccgg tcggcaccag    3296
ttgcgtgagc ggaaagatgg ccgcttcccg gccctgctcc aggggctca aaatggagga    3356 cgcggcgctc gggagagcgg gcgggtgagt cacccacaca aaggaaaagg gcctttccgt   3416
cctcagccgt cgcttcatgt gactccacgg agtaccgggc gccgtccagg cacctcgatt    3476
agttctggag cttttggagt acgtcgtctt taggttgggg ggaggggttt tatgcgatgg    3536 agtttccca cactgagtgg gtggagactg aagttaggcc agcttggcac ttgatgtaat    3596
tctcgttgga atttgccctt tttgagtttg gatcttggtt cattctcaag cctcagacag    3656
tggttcaaag ttttttcctt ccatttcagg tgtcgtgaac acgtggtcgc ggccgcaagc    3716 ttcacc atg aac ttt ctg ctg tct tgg gtg cat tgg agc ctt gcc ttg       3764
       Met Asn Phe Leu Leu Ser Trp Val His Trp Ser Leu Ala Leu
           160                 165 ctg ctc tac ctc cac cat gcc aag tgg tcc cag gct gca ccc atg gca      3812
Leu Leu Tyr Leu His His Ala Lys Trp Ser Gln Ala Ala Pro Met Ala
170                 175                 180                 185 gaa gga gga ggg cag aat cat cac gaa gtg gtg aag ttc atg gat gtc      3860
```

```
Glu Gly Gly Gly Gln Asn His His Glu Val Val Lys Phe Met Asp Val
            190                 195                 200 tat cag cgc agc tac tgc cat cca atc gag acc ctg gtg gac atc ttc    3908
Tyr Gln Arg Ser Tyr Cys His Pro Ile Glu Thr Leu Val Asp Ile Phe
            205                 210                 215 cag gag tac cct gat gag atc gag tac atc ttc aag cca tcc tgt gtg    3956
Gln Glu Tyr Pro Asp Glu Ile Glu Tyr Ile Phe Lys Pro Ser Cys Val
            220                 225                 230 ccc ctg atg cga tgc ggg ggc tgc tgc aat gac gag ggc ctg gag tgt    4004
Pro Leu Met Arg Cys Gly Gly Cys Cys Asn Asp Glu Gly Leu Glu Cys
            235                 240                 245 gtg ccc act gag gag tcc aac atc acc atg cag att atg cgg atc aaa    4052
Val Pro Thr Glu Glu Ser Asn Ile Thr Met Gln Ile Met Arg Ile Lys
250                 255                 260                 265 cct cac caa ggc cag cac ata gga gag atg agc ttc cta cag cac aac    4100
Pro His Gln Gly Gln His Ile Gly Glu Met Ser Phe Leu Gln His Asn
                270                 275                 280 aaa tgt gaa tgc aga cca aag aaa gat aga gca aga caa gaa aat ccc    4148
Lys Cys Glu Cys Arg Pro Lys Lys Asp Arg Ala Arg Gln Glu Asn Pro
            285                 290                 295 tgt ggg cct tgc tca gag cgg aga aag cat ttg ttt gta caa gat ccg    4196
Cys Gly Pro Cys Ser Glu Arg Arg Lys His Leu Phe Val Gln Asp Pro
            300                 305                 310 cag acg tgt aaa tgt tcc tgc aaa aac aca gac tcg cgt tgc aag gcg    4244
Gln Thr Cys Lys Cys Ser Cys Lys Asn Thr Asp Ser Arg Cys Lys Ala
            315                 320                 325 agg cag ctt gag tta aac gaa cgt act tgc aga tgt gac aag ccg agg    4292
Arg Gln Leu Glu Leu Asn Glu Arg Thr Cys Arg Cys Asp Lys Pro Arg
330                 335                 340                 345 cgg tga tctagagttt aaacccgctg atcagcctcg actgtgcctt ctagttgcca     4348
Arg gccatctgtt gtttgcccct cccccgtgcc ttccttgacc ctggaaggtg ccactcccac    4408
tgtcctttcc taataaaatg aggaaattgc atcgcattgt ctgagtaggt gtcattctat    4468
tctgggggt ggggtggggc aggacagcaa gggggaggat tgggaagaca atagcaggca    4528
tgctggggat gcggtgggct ctatggcttc tgaggcggaa agaaccagtg gcggtaatac    4588
ggttatccac agaatcaggg gataacgcag gaaagaacat gtgagcaaaa ggccagcaaa    4648
aggccaggaa ccgtaaaaag gccgcgttgc tggcgttttt ccataggctc cgcccccctg    4708
acgagcatca aaaaatcga cgctcaagtc agaggtggcg aaacccgaca ggactataaa    4768
gataccaggc gtttccccct ggaagctccc tcgtgcgctc tcctgttccg accctgccgc    4828
ttaccggata cctgtccgcc tttctccctt cgggaagcgt ggcgctttct catagctcac    4888
gctgtaggta tctcagttcg gtgtaggtcg ttcgctccaa gctgggctgt gtgcacgaac    4948
ccccgttca gcccgaccgc tgcgccttat ccggtaacta tcgtcttgag tccaacccgg    5008
taagacacga cttatcgcca ctggcagcag ccactggtaa caggattagc agagcgaggt    5068
atgtaggcgg tgctacagag ttcttgaagt ggtggcctaa ctacggctac actagaagga    5128
cagtatttgg tatctgcgct ctgctgaagc cagttacctt cggaaaaaga gttggtagct    5188
cttgatccgg caaacaaacc accgctggta gcggtggttt ttttgtttgc aagcagcaga    5248
ttacgcgcag aaaaaaagga tctcaagaag atcctttgat cttttctacg gggtctgacg    5308
ctcagtggaa cgaaaactca cgttaaggga ttttggtcat gacattaacc tataaaaata    5368
ggcgtatcac gaggcccttt cgtctcgcgc gtttcggtga tgacggtgaa aacctctgac    5428
acatgcagct cccggagacg gtcacagctt gtctgtaagc ggatgccggg agcagacaag    5488
```

```
cccgtcaggg cgcgtcagcg ggtgttggcg ggtgtcgggg ctggcttaac tatgcggcat    5548
cagagcagat tgtactgaga gtgcaccata tatgcggtgt gaaataccgc acagatgcgt    5608
aaggagaaaa taccgcatca ggcgccattc gccattcagg ctgcgcaact gttgggaagg    5668
gcgatcggtg cgggcctctt cgctattacg cca                                5701
```

<210> SEQ ID NO 2
<211> LENGTH: 155
<212> TYPE: PRT
<213> ORGANISM: Artificial Sequence
<220> FEATURE:
<223> OTHER INFORMATION: Synthetic Construct

<400> SEQUENCE: 2

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 3
<211> LENGTH: 191
<212> TYPE: PRT
<213> ORGANISM: Artificial Sequence
<220> FEATURE:
<223> OTHER INFORMATION: Synthetic Construct

<400> SEQUENCE: 3

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

```
Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 4
<211> LENGTH: 5701
<212> TYPE: DNA
<213> ORGANISM: artificial
<220> FEATURE:
<223> OTHER INFORMATION: pBUDK-coVEGF165-coFGF2 plasmid
<220> FEATURE:
<221> NAME/KEY: misc_feature
<222> LOCATION: (670)..(694)
<223> OTHER INFORMATION: Gateway site
<220> FEATURE:
<221> NAME/KEY: misc_feature
<222> LOCATION: (695)..(698)
<223> OTHER INFORMATION: Kozak sequence
<220> FEATURE:
<221> NAME/KEY: CDS
<222> LOCATION: (699)..(1166)
<223> OTHER INFORMATION: FGF2 Gene cDNA
<220> FEATURE:
<221> NAME/KEY: misc_feature
<222> LOCATION: (1167)..(1191)
<223> OTHER INFORMATION: Gateway site
<220> FEATURE:
<221> NAME/KEY: misc_feature
<222> LOCATION: (1470)..(2511)
<223> OTHER INFORMATION: subcloning of Kan resistance gene and promoter
      from pDONR221 in reverse compliment orientation.
<220> FEATURE:
<221> NAME/KEY: misc_feature
<222> LOCATION: (3713)..(3718)
<223> OTHER INFORMATION: Restriction sites HindIII-XbaI
<220> FEATURE:
<221> NAME/KEY: misc_feature
<222> LOCATION: (3719)..(3722)
<223> OTHER INFORMATION: Kozak sequence
<220> FEATURE:
<221> NAME/KEY: CDS
<222> LOCATION: (3723)..(4298)
<223> OTHER INFORMATION: VEGF165 after codon optimization
<220> FEATURE:
<221> NAME/KEY: misc_feature
<222> LOCATION: (4299)..(4304)
<223> OTHER INFORMATION: Restriction sites HindIII-XbaI

<400> SEQUENCE: 4
gcgcgcgttg acattgatta ttgactagtt attaatagta atcaattacg gggtcattag      60
ttcatagccc atatatggag ttccgcgtta cataacttac ggtaaatggc ccgcctggct     120
gaccgcccaa cgacccccgc ccattgacgt caataatgac gtatgttccc atagtaacgc     180
caatagggac tttccattga cgtcaatggg tggactattt acggtaaact gcccacttgg     240
cagtacatca agtgtatcat atgccaagta cgccccctat tgacgtcaat gacgtaaat     300 ggcccgcctg gcattatgcc cagtacatga ccttatggga ctttcctact tggcagtaca     360
tctacgtatt agtcatcgct attaccatgg tgatgcggtt ttggcagtac atcaatgggc     420
gtggatagcg gtttgactca cggggatttc caagtctcca ccccattgac gtcaatggga     480
```

```
gtttgttttg gcaccaaaat caacgggact ttccaaaatg tcgtaacaac tccgccccat    540
tgacgcaaat gggcggtagg cgtgtacggt gggaggtcta taagcaga gctctctggc     600 taactagaga acccactgct tactggctta tcgaaattaa tacgactcac tatagggaga    660
cccaagctta caagtttgta caaaaaagca ggctcacc atg gcc gct gga agc att    716
                                          Met Ala Ala Gly Ser Ile
                                          1               5 acc aca ctg ccc gca ctg ccc gag gat gga ggc tca ggc gca ttc ccc      764
Thr Thr Leu Pro Ala Leu Pro Glu Asp Gly Gly Ser Gly Ala Phe Pro
            10                  15                  20 ccc gga cat ttc aag gac cca aag aga ctg tac tgc aaa aac ggc ggg      812
Pro Gly His Phe Lys Asp Pro Lys Arg Leu Tyr Cys Lys Asn Gly Gly
        25                  30                  35 ttc ttt ctg agg atc cac cca gac gga agg gtg gat ggc gtc cgc gag      860
Phe Phe Leu Arg Ile His Pro Asp Gly Arg Val Asp Gly Val Arg Glu
    40                  45                  50 aag agc gac cct cat atc aaa ctg cag ctg cag gca gag gaa agg ggc      908
Lys Ser Asp Pro His Ile Lys Leu Gln Leu Gln Ala Glu Glu Arg Gly
55                  60                  65                  70 gtg gtc tct att aag ggc gtg tgc gcc aac cga tat ctg gct atg aag      956
Val Val Ser Ile Lys Gly Val Cys Ala Asn Arg Tyr Leu Ala Met Lys
                75                  80                  85 gag gac ggc cgg ctg ctg gcc tct aaa tgc gtc act gat gaa tgt ttc     1004
Glu Asp Gly Arg Leu Leu Ala Ser Lys Cys Val Thr Asp Glu Cys Phe
            90                  95                 100 ttt ttc gag cgc ctg gaa agt aac aat tac aat acc tat cgg agc aga     1052
Phe Phe Glu Arg Leu Glu Ser Asn Asn Tyr Asn Thr Tyr Arg Ser Arg
        105                 110                 115 aaa tac aca tcc tgg tat gtg gct ctg aag cga acc ggg cag tac aaa     1100
Lys Tyr Thr Ser Trp Tyr Val Ala Leu Lys Arg Thr Gly Gln Tyr Lys
    120                 125                 130 ctg gga tcc aaa acc gga ccc ggc cag aag gct atc ctg ttc ctg cca     1148
Leu Gly Ser Lys Thr Gly Pro Gly Gln Lys Ala Ile Leu Phe Leu Pro
135                 140                 145                 150 atg tca gca aaa tct tga acccagcttt cttgtacaaa gtggtgtttg            1196
Met Ser Ala Lys Ser
                155 atccccggga attcagacat gataagatac attgatgagt ttggacaaac cacaactaga   1256 atgcagtgaa aaaatgctt tatttgtgaa atttgtgatg ctattgcttt atttgtaacc    1316 attataagct gcaataaaca agttggggtg ggcgaagaac tccagcatga atccccgcg    1376 ctggaggatc atccagccgg cgtcccggaa aacgattccg aagcccaacc tttcatagaa   1436 ggcggcggtg gaatcgaaat ctcgtagcac gtggtctgac gctcagtgga acgacgcgta   1496 actcacgtta agggattttg gtcatgagct tgcgccgtcc cgtcaagtca gcgtaatgct   1556 ctgccagtgt tacaaccaat taaccaattc tgattagaaa aactcatcga gcatcaaatg   1616 aaactgcaat ttattcatat caggattatc aataccatat ttttgaaaaa gccgtttctg   1676 taatgaagga gaaaactcac cgaggcagtt ccataggatg caagatcct ggtatcggtc    1736 tgcgattccg actcgtccaa catcaataca acctattaat ttcccctcgt caaaaataag   1796 gttatcaagt gagaaatcac catgagtgac gactgaatcc ggtgagaatg caaaagttt    1856 atgcatttct ttccagactt gttcaacagg ccagccatta cgctcgtcat caaaatcact   1916 cgcatcaacc aaaccgttat tcattcgtga ttgcgcctga gcgagacgaa atacgcgatc   1976 gctgttaaaa ggacaattac aaacaggaat cgaatgcaac cggcgcagga acactgccag   2036 cgcatcaaca atattttcac ctgaatcagg atattcttct aatacctgga atgctgtttt   2096
```

```
tccggggatc gcagtggtga gtaaccatgc atcatcagga gtacggataa aatgcttgat    2156
ggtcggaaga ggcataaatt ccgtcagcca gtttagtctg accatctcat ctgtaacatc    2216
attggcaacg ctacctttgc catgtttcag aaacaactct ggcgcatcgg gcttcccata    2276
caagcgatag attgtcgcac ctgattgccc gacattatcg cgagcccatt tatacccata    2336
taaatcagca tccatgttgg aatttaatcg cggcctcgac gtttcccgtt gaatatggct    2396
cataacaccc cttgtattac tgtttatgta agcagacagt tttattgttc atgatgatat    2456
tattttatct tgtgcaatgt aacatcagag attttgagac acgggccaga gctgctcgtc    2516
gagctagctt cgtgaggctc cggtgcccgt cagtgggcag agcgcacatc gcccacagtc    2576
cccgagaagt tgggggagg ggtcggcaat tgaaccggtg cctagagaag gtggcgcggg     2636
gtaaactggg aaagtgatgt cgtgtactgg ctccgccttt ttcccgaggg tggggagaa     2696
ccgtatataa gtgcagtagt cgccgtgaac gttcttttc gcaacgggtt tgccgccaga     2756
acacaggtaa gtgccgtgtg tggttcccgc gggcctggcc tctttacggg ttatggccct    2816
tgcgtgcctt gaattacttc cacctggctc cagtacgtga ttcttgatcc cgagctggag    2876
ccaggggcgg gccttgcgct ttaggagccc cttcgcctcg tgcttgagtt gaggcctggc    2936
ctgggcgctg gggccgccgc gtgcgaatct ggtggcacct tcgcgcctgt ctcgctgctt    2996
tcgataagtc tctagccatt taaaatttt gatgacctgc tgcgacgctt ttttctggc     3056
aagatagtct tgtaaatgcg ggccaggatc tgcacactgg tatttcggtt tttgggcccg    3116
cggccggcga cggggcccgt gcgtcccagc gcacatgttc ggcgaggcgg ggcctgcgag    3176
cgcggccacc gagaatcgga cgggggtagt ctcaagctgg ccggcctgct ctggtgcctg    3236
gcctcgcgcc gccgtgtatc gccccgcct gggcggcaag gctggccgg tcggcaccag     3296
ttgcgtgagc ggaaagatgg ccgcttcccg gccctgctcc aggggggctca aaatggagga   3356
cgcggcgctc gggagagcgg gcgggtgagt cacccacaca aaggaaaagg gcctttccgt    3416
cctcagccgt cgcttcatgt gactccacgg agtaccgggc gccgtccagg cacctcgatt    3476
agttctggag cttttggagt acgtcgtctt taggttgggg ggagggggttt tatgcgatgg   3536
agtttcccca cactgagtgg gtggagactg aagttaggcc agcttggcac ttgatgtaat    3596
tctcgttgga atttgccctt tttgagtttg gatcttggtt cattctcaag cctcagacag    3656
tggttcaaag ttttttttctt ccatttcagg tgtcgtgaac acgtggtcgc ggccgcaagc   3716
ttcacc atg aac ttt ctg ctg tct tgg gtc cac tgg tca ctg gct ctg       3764
       Met Asn Phe Leu Leu Ser Trp Val His Trp Ser Leu Ala Leu
           160                 165
ctg ctg tat ctg cat cac gct aaa tgg agt cag gcc gcc cct atg gcc      3812
Leu Leu Tyr Leu His His Ala Lys Trp Ser Gln Ala Ala Pro Met Ala
170                 175                 180                 185
gag ggc ggg gga cag aac cac cat gaa gtg gtc aag ttc atg gac gtg      3860
Glu Gly Gly Gly Gln Asn His His Glu Val Val Lys Phe Met Asp Val
            190                 195                 200
tac cag aga tca tat tgt cac cct atc gag aca ctg gtc gac att ttc      3908
Tyr Gln Arg Ser Tyr Cys His Pro Ile Glu Thr Leu Val Asp Ile Phe
        205                 210                 215
cag gaa tac cca gat gag atc gaa tat atc ttc aag cca agc tgc gtg      3956
Gln Glu Tyr Pro Asp Glu Ile Glu Tyr Ile Phe Lys Pro Ser Cys Val
    220                 225                 230
cca ctg atg cga tgc gga gga tgc tgt aac gat gag ggg ctg gaa tgc      4004
Pro Leu Met Arg Cys Gly Gly Cys Cys Asn Asp Glu Gly Leu Glu Cys
235                 240                 245
```

```
gtc ccc acc gag gaa tct aat atc aca atg cag atc atg cga att aag      4052
Val Pro Thr Glu Glu Ser Asn Ile Thr Met Gln Ile Met Arg Ile Lys
250             255                 260                 265 cct cac cag gga cag cat att ggc gag atg agt ttc ctg cag cac aac      4100
Pro His Gln Gly Gln His Ile Gly Glu Met Ser Phe Leu Gln His Asn
            270                 275                 280 aaa tgc gag tgt cgg cca aag aaa gac agg gct cgc cag gag aat ccc      4148
Lys Cys Glu Cys Arg Pro Lys Lys Asp Arg Ala Arg Gln Glu Asn Pro
        285                 290                 295 tgt ggc cct tgc tct gaa cgg aga aag cat ctg ttt gtg cag gac ccc      4196
Cys Gly Pro Cys Ser Glu Arg Arg Lys His Leu Phe Val Gln Asp Pro
    300                 305                 310 cag act tgc aag tgt agc tgc aaa aat acc gat tcc agg tgt aaa gca      4244
Gln Thr Cys Lys Cys Ser Cys Lys Asn Thr Asp Ser Arg Cys Lys Ala
315                 320                 325 cgg cag ctg gaa ctg aac gaa agg acc tgt cga tgt gat aaa cca agg      4292
Arg Gln Leu Glu Leu Asn Glu Arg Thr Cys Arg Cys Asp Lys Pro Arg
330                 335                 340                 345 aga taa tctagagttt aaacccgctg atcagcctcg actgtgcctt ctagttgcca      4348
Arg gccatctgtt gtttgcccct cccccgtgcc ttccttgacc ctggaaggtg ccactcccac    4408
tgtcctttcc taataaaatg aggaaattgc atcgcattgt ctgagtaggt gtcattctat    4468 tctgggggt ggggtggggc aggacagcaa ggggaggat tgggaagaca atagcaggca      4528
tgctggggat gcggtgggct ctatggcttc tgaggcggaa agaaccagtg gcggtaatac    4588
ggttatccac agaatcaggg gataacgcag gaaagaacat gtgagcaaaa ggccagcaaa    4648
aggccaggaa ccgtaaaaag gccgcgttgc tggcgttttt ccataggctc cgcccccctg    4708
acgagcatca caaaaatcga cgctcaagtc agaggtggcg aaacccgaca ggactataaa    4768
gataccaggc gtttccccct ggaagctccc tcgtgcgctc tcctgttccg accctgccgc    4828
ttaccggata cctgtccgcc tttctccctt cgggaagcgt ggcgctttct catagctcac    4888
gctgtaggta tctcagttcg gtgtaggtcg ttcgctccaa gctgggctgt gtgcacgaac    4948
cccccgttca gcccgaccgc tgcgccttat ccggtaacta tcgtcttgag tccaacccgg    5008
taagacacga cttatcgcca ctggcagcag ccactggtaa caggattagc agagcgaggt    5068
atgtaggcgg tgctacagag ttcttgaagt ggtggcctaa ctacggctac actagaagga    5128
cagtatttgg tatctgcgct ctgctgaagc cagttacctt cggaaaaaga gttggtagct    5188
cttgatccgg caaacaaacc accgctggta gcggtggttt ttttgtttgc aagcagcaga    5248
ttacgcgcag aaaaaaagga tctcaagaag atcctttgat cttttctacg gggtctgacg    5308
ctcagtggaa cgaaaactca cgttaaggga ttttggtcat gacattaacc tataaaaata    5368
ggcgtatcac gaggcccttt cgtctcgcgc gtttcggtga tgacggtgaa aacctctgac    5428
acatgcagct cccggagacg gtcacagctt gtctgtaagc ggatgccggg agcagacaag    5488
cccgtcaggg cgcgtcagcg ggtgttggcg ggtgtcgggg ctggcttaac tatgcggcat    5548
cagagcagat tgtactgaga gtgcaccata tatgcggtgt gaaataccgc acagatgcgt    5608
aaggagaaaa taccgcatca ggcgccattc gccattcagg ctgcgcaact gttgggaagg    5668
gcgatcggtg cgggcctctt cgctattacg cca                                5701
```

<210> SEQ ID NO 5
<211> LENGTH: 155
<212> TYPE: PRT
<213> ORGANISM: artificial
<220> FEATURE:

<223> OTHER INFORMATION: Synthetic Construct

<400> SEQUENCE: 5

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 6
<211> LENGTH: 191
<212> TYPE: PRT
<213> ORGANISM: artificial
<220> FEATURE:
<223> OTHER INFORMATION: Synthetic Construct

<400> SEQUENCE: 6

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160
```

-continued

```
Cys Lys Cys Ser Cys Lys Asn Thr Asp Ser Arg Cys Lys Ala Arg Gln
            165                 170                 175

Leu Glu Leu Asn Glu Arg Thr Cys Arg Cys Asp Lys Pro Arg Arg
            180                 185                 190
```

CODON-OPTIMIZED RECOMBINANT PLASMID, METHOD OF STIMULATING PERIPHERAL NERVE REGENERATION, AND METHOD OF TREATING NERVE DAMAGE IN HUMANS

CROSS REFERENCE TO RELATED APPLICATIONS

This application is a continuation-in-part of U.S. application Ser. No. 15/460,668, filed Mar. 16, 2017, which is a continuation of application PCT/RU2015/000545, filed Aug. 27, 2015, which claims priority to application RU2014137218, filed Sep. 16, 2014, all of which are incorporated herein by reference in their entireties.

BACKGROUND OF THE INVENTION

Field of Invention

The present invention is in the field of medicine and more specifically in the fields of neurosurgery, traumatology and maxillofacial surgery as applied to treatment of peripheral nerve injuries. These injuries are effectively treated with engineered recombinant nucleic acids. One example of such an engineered recombinant nucleic acid is a plasmid that encodes and expresses vascular endothelial growth factor (VEGF) and fibroblast growth factor 2 (FGF2) when contacted with or transformed into a tissue.

Discussion of the Background

About 3-10% of the population sustains peripheral nervous system injuries [1-3]. Peripheral nerve injuries are a common cause of occupational disability and such injuries not only incapacitate numerous workers or working age individuals, but reduce the quality of life. Rehabilitation of a peripheral nerve injury can require a prolonged period of treatment including periods of a year or longer. Photographs of peripheral nervous system injuries and their symptoms are shown by the Figures.

Existing methods for treating peripheral nervous system injuries depend on the extent and nature of the injury in a particular individual including a mechanism of the injury, extent of the peripheral nervous system defect, distance from the location of the injury of the peripheral nerve to the innervated area, and the time elapsed between the injury and surgical intervention.

One type of the reconstructive treatment involves reconnection of the incised nerve ends by means of the end-to-end anastomosis. Peripheral nerve injuries are often accompanied by the formation of prolonged defects, thereby rendering this approach inapplicable. In such cases, autologous nerve grafting is the most appropriate option for repairing prolonged nerve defects. A nerve that is less functionally significant can be used as an autologous graft. Another treatment involves replacement of a peripheral nervous system tissue defect with various structures that create conditions for peripheral nerve regeneration, such as a tubular structure that is designed to replace an extended tissue defect and foster peripheral nerve regeneration. However, despite the advances in reconstructive techniques to restore the peripheral nerve integrity only a partial recovery of the function of an innervated extremity usually occurs even under the most favorable conditions.

These limitations of conventional modes of treating peripheral nervous system injuries necessitate a further search for new methods that enhance results of standard reconstructive treatment, reduce morbidity, disability and generally improve quality of patient's life.

One concept under study involves use of growth factors to induce regeneration of a peripheral nerve. This concept has resulted from the accumulation of knowledge about the roles various growth factors play in the natural process of peripheral nerve health, growth, and regeneration [4].

Vascular endothelial growth factor (VEGF) is one of the well-studied growth factors that affect recovery of peripheral nerves. VEGF is one of the main regulators of angiogenesis and vasculogenesis. It is a disulfide-bound dimeric glycoprotein having an average molecular weight of 34-42 kDa. VEGF-A is a specific mitogen for endothelial cells (ECs) and induces their proliferation, activation, differentiation and formation of EC capillary tubules. These capillary tubules are further remodeled into mature blood vessels. VEGF also induces expression of antiapoptotic proteins and increases survival of ECs. Serious defects and improper development of the cardiovascular system occurs in animals where genes encoding VEGF have been deleted. These defects may be fatal.

A human VEGF is encoded by a gene located on the chromosomal locus 6p21.3. The coding region comprises about 14,000 bps. VEGF has several isoforms including VEGF 121, VEGF 145, VEGF 148, VEGF 165, VEGF 183, VEGF 189, and VEGF 206. These isoforms result from the alternative splicing of VEGF mRNA which consists of 8 exons. Different isoforms of VEGF have biochemical differences in the ability to bind heparin- and heparan-sulphate which permits them to traffic to different extracellular locations. Differences in biochemical properties or extracellular trafficking of human VEGF-A isoforms are attributable to the alternative splicing of exons 6 and 7, because all transcripts of the human VEGF-A gene contain exons 1-5 and 8.

VEGF had long been considered only as an inductor of angiogenesis and as a potential therapeutic agent for treatment of different disorders accompanied by tissue ischemia. However, new data on VEGF's neuroprotective properties for neurons of both the peripheral and central nervous systems have been obtained [5, 6]. VEGF stimulates proliferation of Schwann cells, astrocytes, microglia, and cortical neurons [7-10]. A significant increase of expression of VEGF and Flt-1 (VEGF type II receptor) in the lumbar spine in response to an injury was shown in a rat sciatic nerve crush injury model [11]. The axonal sprouting that manifests as the increased axon number in the conduit per a unit of the cross section area was observed when VEGF was used as a part of the matrigel filling in the conduit [12].

The use of VEGF-loaded poly-lactic acid microspheres in an autologous vein graft in a model of trauma with an extensive defect of fibular and tibial nerves was found to improve the nerve functional index and to increase the number of myelinated fibers in the graft [13].

VEGF has been shown to induce Schwann cell division and migration in a graft towards distal parts that correlates with the increased number of capillaries and myelinated fibers [14].

Introduction of VEGF in combination with a Brain-derived neurotrophic factor (BDNF) into cavernosal bodies in a rat cavernous nerve injury model resulted in the recovery of the lost innervation and erectile function [15].

FGF is another growth factor that induces neurogenesis. FGF induces Schwann cell proliferation and migration in a peripheral nerve injury [16].

In experiments using animal models, it was shown that blocking receptors for FGF, Fgfr1 and Fgfr2, caused neuropathy of non-myelinating sensory fibers and significant impairment of the thermal pain sensitivity [17].

The use of bone marrow-derived stem cells in a peripheral nerve injury model resulted in increased FGF expression that induced migration and proliferation of Schwann cells [18].

In a thoracic spinal cord injury model, the use of FGF in a sciatic nerve graft promoted the improvement of the upper extremity motor function [19].

Therapeutic applications of growth factors, such as VEFG and FGF, were known to have a number of limitations. After the administration into the injury site the growth factors undergo rapid degradation and, therefore, their constant concentration cannot be maintained to achieve the desired therapeutic effect [20].

Gene therapy using vectors that express growth factors like VEGF had previously been performed. There are two main trends in gene therapy: (i) use of viral vectors and (ii) use of non-viral vectors. These different trends generally operate through different mechanisms of gene transfer. The use of viral vectors in the clinical setting, despite their high transfection activity, is limited due to the risk of insertional mutagenesis and potential induction of the inflammatory response and toxicity.

A safer method of gene transfer is based on the use of plasmid DNA. In a model of musculocutaneous nerve repair with end-to-end and end-to-side anastomosis, intraoperative administration of a DNA plasmid comprising a vegf gene into a distal region resulted in the significantly increased number of myelinated fibers per a unit of the cross-section area of the region distal to the anastomosis site that correlated with a significant increase of the VEGF concentration in Schwann cells [21].

A gene-therapeutic construction could be injected paraneurally. In a sciatic nerve injury model, plVEGF was administrated intramuscularly and was combined with a hyaluronic acid film sheath which covered the anastomosis site in order to reduce severity of the scarring. The drug intramuscular injection was accompanied by a significant increase of the muscular response amplitude and the increased number of myelinated fibers distal to the anastomosis site against their use as monotherapy [22].

The study performed by Wang F. et al. demonstrated a plVEGF dose-dependent effect when the gene therapeutic construction was given intraneurally after the end-to-end suturing of sciatic nerve stumps. The use of a higher dosage resulted in the most pronounced increase of neurophysiological parameters and a lesser decrease of the calf muscle weight index [23].

Synergism in action of some factors has been uncovered. For example, combined use of a VEGF gene-coding plasmid and a plasmid encoding the C—CSF gene in a sciatic nerve injury model demonstrated a more pronounced increase in the number of myelinated fibers and capillaries in the region distal to the end-to-end anastomosis, maintenance of more neurons in the spinal ganglia as well as the early recovery of the motor function [24]. However, only a part of the cells is transfected with plasmid DNA when using gene therapeutic agents in vivo. Consequently, the probability that a cell is transfected simultaneously with two different gene therapeutic constructions is reduced. The efficacy of a combination of genetic sequences of two growth factors having a synergistic action in one plasmid has been demonstrated in an animal model of the spinal cord contusion injury.

During this experiment it had been shown that when 40 µg of a VEGF and FGF2 gene containing plasmid were directly injected into the spinal cord, there was a significant increase of the capillary number in the sections made at 1.5 cm from the trauma core. Based on the behavior test data, the recovery of the motor function significantly improved as compared to the control group of animals that were not given the plasmid containing VEGF and FGF2 genes. Based on the results obtained in this experiment, it had been concluded that application of the double cassette plasmid improves spinal cord vascularization and reduces the area of destruction of the spinal gray and white matter [25].

The use of gene therapeutic constructions comprising VEGF and the basic fibroblast growth factor to improve sciatic nerve recovery has been described in [26]. Patent RU 2459630 C1 "Stimulation Technique for Neuroregeneration with Genetic Constructions" describes a method of the post-traumatic regeneration of the rat spinal cord when injecting a double-cassette plasmid pBud-VEGF-FGF2.

Spinal cord and peripheral nerves exhibit significant differences in the regenerative potential. Consequently, the results described above have given no indication as to whether the treatment of a peripheral nerve injury with a plasmid expressing both VEGF and FGF2 could be effective in repairing peripheral nerve injuries. This is due to the fact that the mechanism of a contusion injury significantly differs by pathogenesis and a degree of severity from a trauma accompanied with neurotmesis which is more specific for peripheral nerves and prevails in the total structure of their injuries. Moreover, as mentioned above, the type or extent of regenerative or recuperative effects of applying particular growth factors, or a combination of growth factors, to damaged peripheral nervous system tissue are substantially unexplored.

Keeping in mind these problems with protein-based therapies and uncertainties regarding responsiveness of peripheral nerve injuries to a nucleic-acid based therapy, the inventors have developed nucleic-acid based vectors that express growth factors such as VEGF and FGF2 and initiated studies to determine whether incorporation of these growth factors into a complex therapy of a peripheral nerve repair could be effective. As shown herein, a better, more reliable, and more effective treatment of peripheral nerve injuries is possible using a nucleic acid-based therapy.

SUMMARY OF THE INVENTION

Accordingly, one object of the present invention is to provide a method for treating a peripheral nervous system damage or injury, or for regenerating peripheral nervous system tissue, comprising administering to a subject in need thereof a vector that comprises polynucleotide sequences that encode vascular endothelia growth factor (VEGF) and fibroblast growth factor (FGF2).

In one embodiment, the vector comprises FGF2 encoding nucleotides at positions 699-1166 and VEGF165 encoding nucleotides at positions 3723-4298 of SEQ ID NO: 1 and resistance to kanamycin nucleotides at positions 1469-2511 of SEQ ID NO: 1. In another embodiment, the vector is pBud(Kan)-VEGF-FGF2 (SEQ ID NO: 1).

Another object of the present invention is to provide a vector comprising polynucleotide sequences that encode vascular endothelia growth factor (VEGF), fibroblast growth factor (FGF2), and resistance to kanamycin. In one embodiment, the vector has SEQ ID NO: 1 and comprises FGF2 encoding nucleotides at positions 699-1166, VEGF165 encoding nucleotides at positions 3723-4298 of SEQ ID NO: 1, and resistance to kanamycin nucleotides at positions 1469-2511 of SEQ ID NO: 1.

Another object of the present invention is to provident genetic sequences encoding modified VEGF and FGF-2 that are delivered into tissue using the recombinant plasmid pBud(Kan)-coVEGF165-coFGF2. In one embodiment, the vector pBud(Kan)-coVEGF165-coFGF2 has SEQ ID NO: 4.

Another object of the present invention is to provide a cell that has been transformed with the vector.

BRIEF DESCRIPTION OF THE FIGURES

The patent or application file contains at least one drawing executed in color. Copies of this patent or patent application publication with color drawing(s) will be provided by the office upon request and payment of the necessary fee.

A more complete appreciation of the invention and many of the attendant advantages thereof will be readily obtained as the same becomes better understood by reference to the following detailed description when considered in connection with the accompanying drawings, wherein:

FIG. 15 shows electromyography findings for the hypothenar muscle group.

FIG. 16 A, B, C—show the mmunofluorescence analysis of VEGF and FGF2 expression in genetically modified HEK293T cells 48 hours after transfection by fluorescence microscopy. A) Staining with primary antibodies to FGF2 and secondary antibodies conjugated to the fluorescent label Alexa-488. B) Staining with primary antibodies to VEGF and secondary antibodies conjugated to the fluorescent label Alexa-555. C) Staining with a fluorescent dye DAPI and matching the fluorescence of FGF2 and VEGF. Scale: 50 μm.

DETAILED DESCRIPTION OF THE INVENTION

Figure 1:
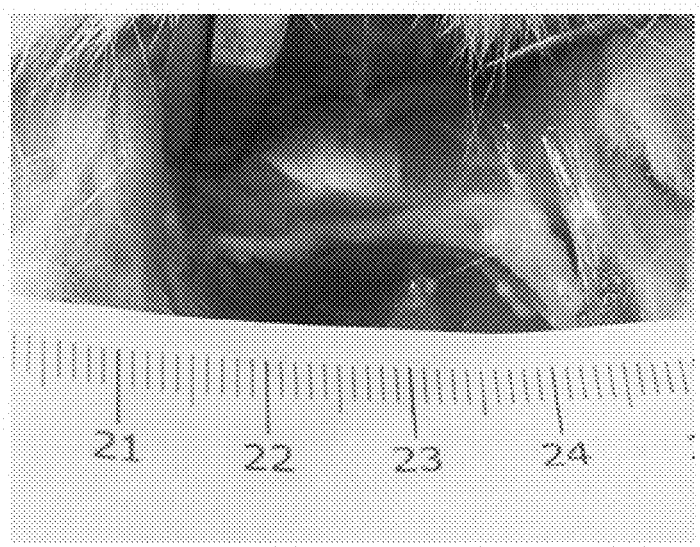
FIG. 1 provides the repeated approach. The entire sciatic nerve with an autologous graft is visualized. Results after injection of plasmid pBud(Kan)-VEGF-FGF2.

The present invention is used in medicine, preferably in neurosurgery, traumatology and maxillofacial surgery, and in treatment of peripheral nerve injuries.

As used herein the words "a", "an" and the like generally carry a meaning of "one or more", unless stated otherwise.

A goal of the inventors' research has been to create, based on their experience in the development of gene therapeutic agents, an effective product for treating patients with peripheral nerve injuries. For this purpose, the inventors have developed various gene therapeutic constructions that differ from each other by the number of encoded transgenes and the transgenes, as well as by the nucleotide sequences of the same transgenes.

In one embodiment, an object of the present invention is to provide an improved or enhanced method for reconstructive treatment involving delivery of a therapeutic polynucleotide construct into or in the vicinity of a damaged peripheral nervous system tissue. An example of this embodiment is the delivery of genetic sequences encoding VEGF and FGF-2 into such tissue using the recombinant plasmid pBud(Kan)-VEGF-FGF2. In another embodiment, genetic sequences encoding modified VEGF and FGF-2 are delivered into such tissue using the recombinant plasmid pBud (Kan)-coVEGF165-coFGF2.

An object of the present invention is to provide a method for treating a peripheral nervous system damage or injury, or for regenerating peripheral nervous system tissue, comprising administering to a subject in need thereof a vector that comprises polynucleotide sequences that encode vascular endothelia growth factor (VEGF) and fibroblast growth factor (FGF2).

A range of the injected plasmid could be from 200 to 500 μg per nerve in 2.5 ml of a physiologic saline solution. The ranges include all values and subranges therebetween, including 250, 300, 350, 400, and 450 μg per nerve in 2.5 ml of a physiologic saline solution and any amount in between.

The vector could be administered in vivo. In another embodiment, the vector is administered to a site of the peripheral nervous system damage or injury or to a tissue to be regenerated. In a different embodiment, the vector is administered to a site of the peripheral nervous system damage or injury at a site proximal or distal to the peripheral nervous system damage, or at sites proximal and distal to said damage. The vector could be administered intra-, peri- and/or paraneurally.

In yet another embodiment, the vector is contacted with a neuron or a Schwann cell, astrocyte, microglia and/or neuron.

In one embodiment, the subject has neurotmesis. In another embodiment, the subject has a diastatic peripheral nerve damage. In a different embodiment, the subject has peripheral nerve damage other than neurotmesis or diastatic peripheral nerve damage. The subject could be human or animal.

In one embodiment, the vector comprises a polynucleotide sequence that encodes resistance to kanamycin.

In another embodiment, the vector comprises FGF2 encoding nucleotides at positions 699-1166 and VEGF165 encoding nucleotides at positions 3723-4298 of SEQ ID NO: 1. The vector further could comprise resistance to kanamycin nucleotides at positions 1469-2511 of SEQ ID NO: 1. In yet another embodiment, the vector is pBud(Kan)-VEGF-FGF2 that has SEQ ID NO: 1.

In another embodiment, a vector comprises codon optimized polynucleotide sequences that encode vascular endothelia growth factor (coVEGF) and codon optimized fibroblast growth factor (coFGF2), and resistance to kanamycin. In one embodiment, the vector is pBud(Kan)-coVEGF165-coFGF2 that has SEQ ID NO: 4. In one embodiment, the vector comprises coFGF2 encoding nucleotides at positions 699-1166 and coVEGF165 encoding nucleotides at positions 3723-4298 of SEQ ID NO: 4. The vector further could comprise resistance to kanamycin nucleotides at positions 1469-2511 of SEQ ID NO: 4.

A different object of the present invention is to provide a cell that has been transformed with the vectors.

Having generally described this invention, a further understanding can be obtained by reference to certain specific examples which are provided herein for purposes of illustration only and are not intended to be limiting unless otherwise specified.

EXAMPLES

Comparative Example 1. Treatment of Diastatic Peripheral Nerve Injury with VEGF/FGF2 Gene Therapy An animal model of a diastatic peripheral nerve injury was used to evaluate effects of gene therapy with the plasmid vector encoding both VEGF and FGF2 described by Masgutov [26].

Test animals (rats), were divided into three groups: (i) intact group, (ii) a test group where a gene therapeutic construction was administered, and (iii) a control group where a phosphate-buffered saline (PBS) solution was injected instead of the gene therapeutic construction.

In test group (ii) a total dose of 45 μg of a gene therapeutic construction was directly injected equally into distal and proximal ends of an autologous nerve graft. In control group (iii) a phosphate-buffered saline (PBS) solution was injected into these locations instead of the gene therapeutic construction.

The evaluation criteria of the regeneration dynamics of the peripheral nerve included neurophysiological parameters such as the nerve conduction velocity and the muscle response amplitude as well as the histological examination findings such as the number of myelinated fibers and the capillary network density.

On day 56 following the injection of the plasmid construction, the neurophysiological parameters in the test group (ii) were superior to those in the control group (iii); however, they were significantly inferior to those in the intact animals of group (i).

A histological examination revealed that myelinated fiber numbers per unit of the cross-section area of the graft were significantly higher in the experimental group (ii) compared to the control group (iii). However, no effective recovery of the extremity function was observed. These experiment results show that the use of plasmid-based constructions containing genetic sequences of growth factors provides a stimulating effect on the regeneration of peripheral nerves.

Example 1. Construction and Evaluation of Vector Encoding VEGF and FGF2 in Animal Model The inventors have sought to determine whether the effect observed in Comparative Example 1 was attributable to the construction of the used plasmid. The inventors have engineered a new plasmid encoding VEGF and FGF2 which replaced the tag sequences in the prior vector with a gene encoding kanamycin resistance. Among other constructs, plasmid pBud(Kan)-VEGF-FGF2 (SEQ ID NO: 1) was constructed. This plasmid has been engineered to include a sequence encoding resistance to kanamycin at nucleotides 1469-2511 of SEQ ID NO: 1; cDNA of a gene encoding FGF2 at nucleotides 699-1166 in SEQ ID NO: 1; cDNA of the gene encoding VEGF165 at nucleotides 3723-4298 in SEQ ID NO: 1; and the Kozak sequence at nucleotides 695-698 and 3719-3722.

The rat animal model of a peripheral nerve injury substantially as described in Comparative Example 1 was used to evaluate the effect of administering the new plasmid constructs, including plasmid pBud(Kan)-VEGF-FGF2 (SEQ ID NO: 1). Gene therapeutic constructions were administrated intraneurally immediately after the peripheral nerve suturing. The results were evaluated after 60 days following the surgical intervention and therapeutic constructs administration. Of all the plasmid DNAs that were used, the best results were obtained for the plasmid pBud (Kan)-VEGF-FGF2 (SEQ ID NO: 1) containing genetic sequences of FGF2 and VEGF. The results for the plasmid pBud(Kan)-VEGF-FGF2 are depicted by FIG. 1. Based on these favorable non-clinical results, the inventors evaluated whether peripheral nerve regeneration could be attained in the clinical setting using the gene therapeutic construction pBud(Kan)-VEGF-FGF2 (SEQ ID NO: 1), as described below.

Example 2. Clinical Evaluation of Regenerative Effects of pBud(Kan)-VEGF-FGF2 (SEQ ID NO: 1)

Figure 2:
FIG. 2 shows a view of the upper extremity prior to surgery. Post-traumatic and post-operative indented irregular scars are seen on the anterior and posterolateral surfaces of the lower, middle, and upper third of the right upper arm.

Patient B., born in 1985, was admitted to the trauma center of the Republic Clinical Hospital of MoH of the Republic of Tatarstan on Apr. 4, 2011, with the diagnosis of sequelae of the median and ulnar nerve injury in the middle third of the right upper arm as shown by FIG. 2. From the patient's history, it was known that in 2009 the patient had a glass cut of the middle third of the upper arm, with the median and ulnar nerves damaged.

The median and ulnar nerves were sutured end-to-end immediately after the injury. However, both motor and sensitivity functions were completed absent in the immediate post-operation period. A course of rehabilitation therapy had produced no visible results.

After 7 months, in 2010, neurolysis of the median and ulnar nerves was performed due to the lack of positive changes in the motor and sensitivity functional recovery. Slight changes in nerve regeneration were observed in the post-operative follow-up, namely, complete lack of sensitivity, at the same time, the motor function appeared which was characterized by the mild bending of the injured hand and fingers. It was decided to perform a surgical treatment.

Figure 3:
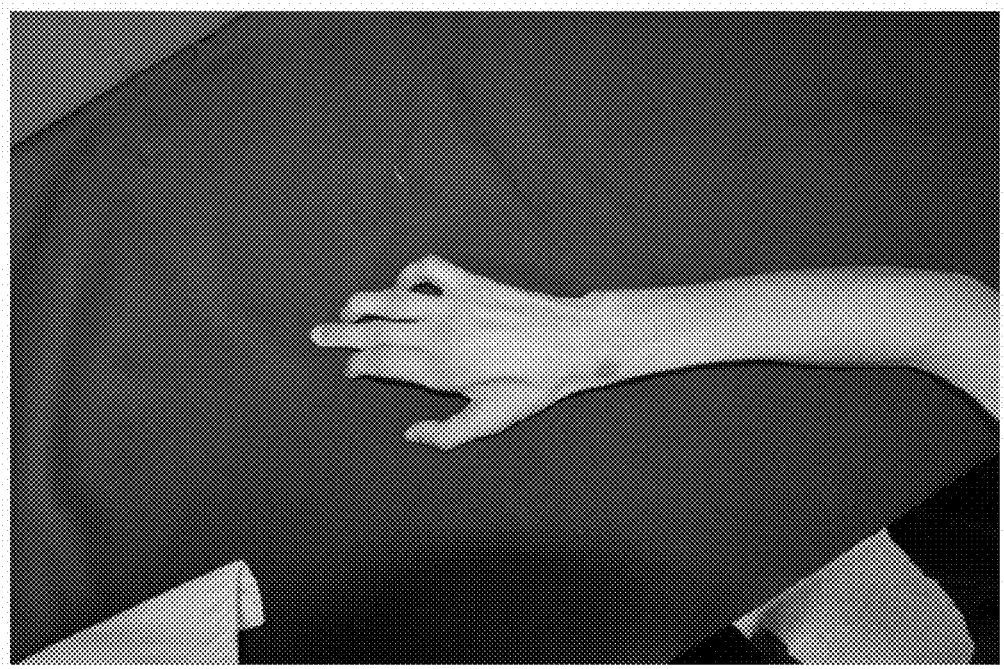
FIG. 3 shows lack of active movements in the middle phalanges of fingers 2-5.

Prior to surgery, on Apr. 21, 2011, the patient had an examination with the following results:

Trophic Disturbances
a) skin status: normal color, decreased fingers' temperature, increased feeling of chillness;
b) atrophy of the hand and forearm muscles, as compared to the normal arm: more than 2 cm as shown by FIGS. 2 and 3.
c) nail changes: hypoplastic; and
d) secretory function (sweating): decreased.

Sensitivity Testing in the Patient in the Autonomous Zone of Innervation by the Nerve:

| No. | Kinds of Sensitivity | Brief Description |
|---|---|---|
| 1. | Pain | Absent |
| 2. | Temperature | Absent |
| 3. | Tactile | Absent |
| 4. | Discriminative | Absent |
| 5. | Sense of two-dimension space | Absent |
| 6. | Stereognosis | Absent |
| 7. | Sense of pressure | Absent |
| 8. | Sense of weight | Absent |

| Degree | Motor function recovery |
|---|---|
| M2 | Distinct contractions without movements in joints |

Motor Function Testing

| Degree | Sensitivity recovery |
|---|---|
| S0 | Lack of sensitivity within the nerve autonomous zone |

Figure 4:
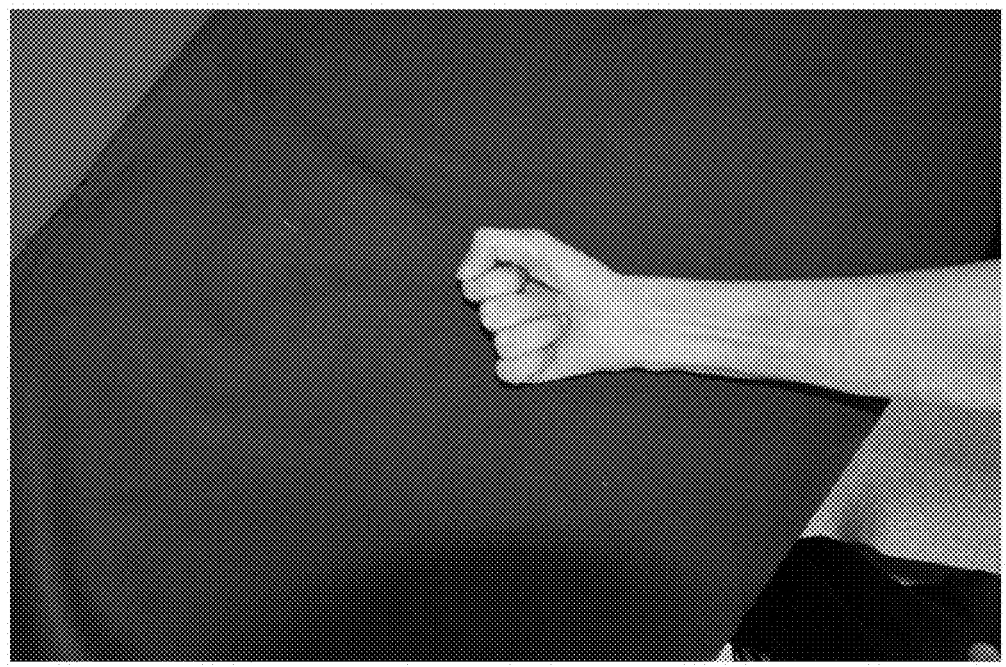
FIG. 4 shows the impaired prehension function by all fingers.

Hand prehension patterns: the hand is unable to perform any type of prehension (FIG. 3-4).

Figure 5:
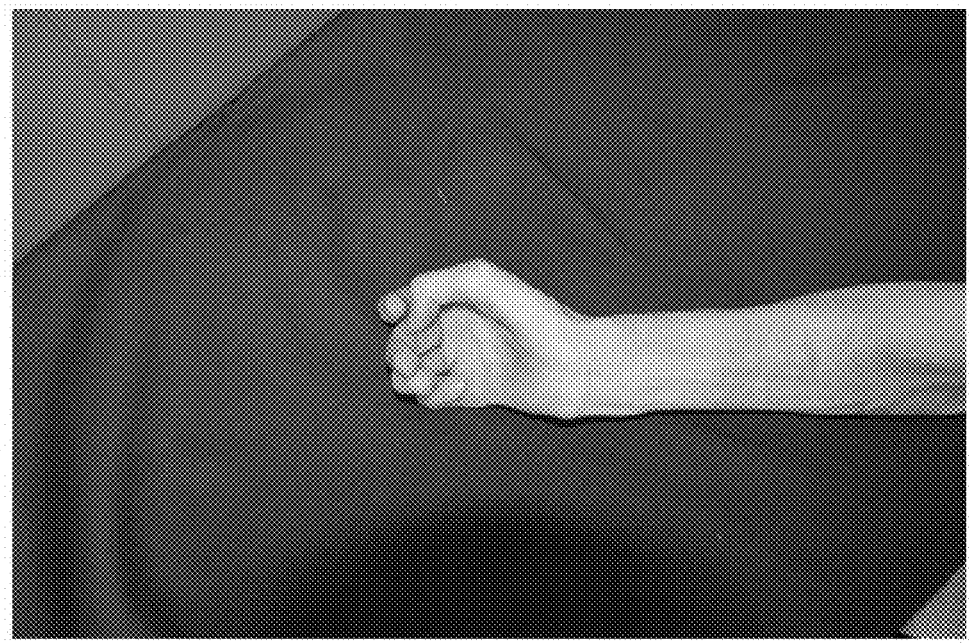
FIG. 5 shows high-grade atrophy of the hand muscle within a zone innervated by the median and ulnar nerves and the ability to oppose finger 1 to finger 2 only.

Diagnosis: the injury of the median and ulnar nerves in the middle third of the forearm sustained 2 years ago. The status post suturing and neurolysis of the median and ulnar nerves are shown in FIG. 5.

A surgery was performed on Apr. 26, 2011, including neurolysis of the median and ulnar nerves with the intraneural administration of plasmid pBud(Kan)-VEGF-FGF2 (SEQ ID NO: 1) containing the vegf and fgf-2 genes.

The surgery was conducted under the nerve block anaesthesia. Following triple treatment of the surgical field, an arcuate incision was made on the inner surface of the right upper arm. The median and ulnar nerves were isolated with technical difficulties. The suture lines had been found. There were no neuroma signs observed; however, the nerves were involved in a scar-forming process and adhered to the surrounding tissue.

Figure 6:
FIG. 6 shows injection of the recombinant plasmid pBud (Kan)-VEGF-FGF2 into the repaired nerve into the suture zone and also proximally and distally over the length of 10 cm.
Figure 7:
FIG. 7 shows application of fibrin glue to prevent leakage of the recombinant plasmid.

The plasmid pBud(Kan)-VEGF-FGF2 was injected with an insulin needle, 250 µg per nerve in 2.5 ml of a physiologic saline solution. The injection was administered into the suture zone and also proximally and distally over the length of 10 cm (FIG. 6). After that 2 ml of the two-component fibrin glue TISSUCOL® was applied to the isolated nerves (FIG. 7).

The post-surgical case included hemostasis, wound suturing, placement of a rubber tube drainage, and application of an antiseptic dressing and a plaster cast. A re-examination was performed one month after the surgery.

Figure 8:
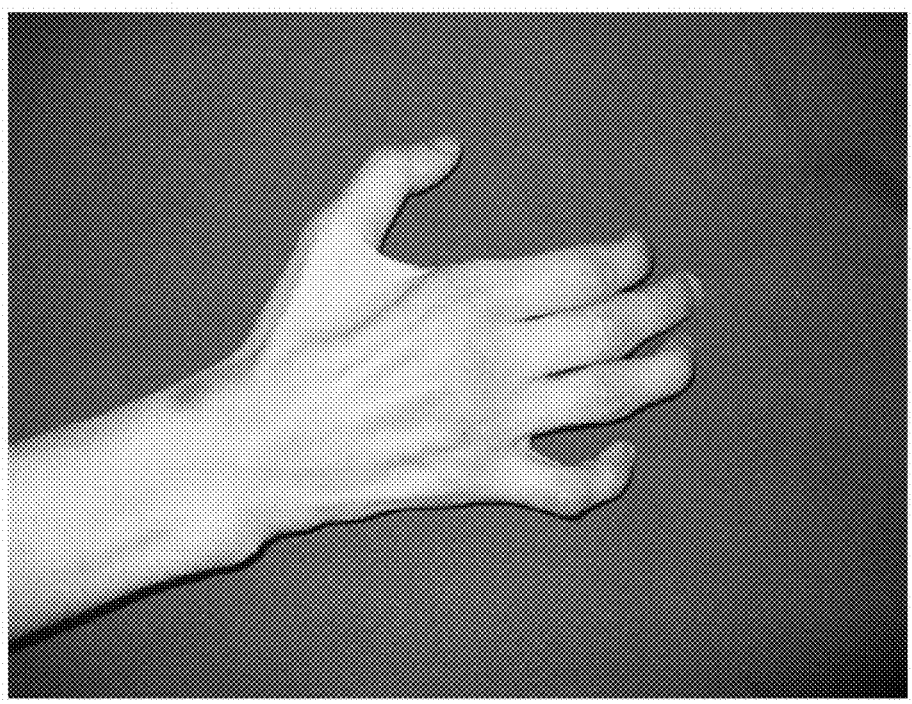
FIG. 8 shows atrophy of hand and forearm muscles. Nail changes: hypoplastic. Secretory function (sweating): decreased. Figure demonstrates post-surgical improvement in patient's condition.

The results of the physical examination dated on May 25, 2011, are presented below:

Trophic Disturbances
a) skin status: normal color;
b) atrophy of the injured hand and forearm muscles, compared to the normal arm: more than 2 cm (FIG. 8);
c) nail changes: hypoplastic; and
d) secretory function (sweating): decreased.

Sensitivity Testing in the Patient in the Autonomous Zone of Innervation by the Nerve:

| No. | Kinds of Sensitivity | Brief Description |
|---|---|---|
| 1. | Pain | Absent |
| 2. | Temperature | Hot - absent |
|  |  | Cold - distal phalanges of fingers 1, 2 |
| 3. | Tactile | Fingers 1, 2 - distal phalange |
| 4. | Discriminative | Absent |
| 5. | Sense of two-dimension space (Moberg pickup test) | Absent |
| 6. | Sense of pressure | Present |
| 7. | Sense of weight | present |

| Degree | Sensitivity recovery |
|---|---|
| S1 | Recovery of deep pain sensitivity within the nerve autonomous zone |

Motor Function Testing

| Degree | Motor function recovery |
|---|---|
| M2 | Distinct contractions without movements in joints |

Hand prehension patterns: the hand is unable to perform any type of prehension.

A regular examination was performed in 6 months after the surgery. The results of the physical examination dated on Nov. 15, 2012, are presented below:

Trophic Disturbances
a) skin status: of normal color;
b) atrophy of the hand and forearm muscles, compared to the normal arm: moderate (1-2 cm) and severe (more than 2 cm);
c) nail changes: within normal limits; and
d) secretory function (sweating): normal.

Sensitivity Testing in the Patient in the Autonomous Zone of Innervation by the Nerve:

| No. | Kinds of Sensitivity | Brief Description |
|---|---|---|
| 1. | Pain | Present, including distal phalanges of all fingers |
| 2. | Temperature | Hot - distal phalanges of finger 1, middle phalanges of fingers 3, 4 |
|  |  | Cold - distal phalanges of fingers 1, 3; distal phalanges of fingers 2, 4, 5 |
| 3. | Tactile | Fingers 1, 3 - distal phalange, middle phalange 2, 4, 5 |

| No. | Kinds of Sensitivity | Brief Description |
|---|---|---|
| 4. | Discriminative | finger 1 - 10 mm |
| | | finger 2 - 30 mm |
| | | finger 3 - 20 mm |
| | | finger 4 - 30 mm |
| | | finger 5 - 30 mm |
| 5. | Sense of two-dimension space (Moberg pickup test) | Identifies large objects (a box of cigarettes, glue, tube for blood collection), a pencil, glue tube |
| 6. | Sense of pressure | Present |
| 7. | Sense of weight | present |

| Degree | Sensitivity recovery |
|---|---|
| S3 | Recovery of surface pain and tactile sensitivity within the entire autonomous zone with complete hyperpathia disappearance |

Motor Function Testing

| Degree | Motor function recovery |
|---|---|
| M3 | Mild movements in joints (useful recovery) |

Hand Prehension Patterns:
1) cylindrical grasp—YES;
2) spherical grasp—YES;
3) hook grasp (a bag handle)—YES;
4) first grasp—YES;
5) tip prehension
   a) terminal opposition—YES;
   b) subterminal opposition—NO;
6) lateral prehension
   a) pinch grip—NO;
   b) scissor grip—"cigarette"—NO.

A year after the surgery, the patient had a regular examination. The results of the physical examination dated on Apr. 20, 2012, are presented below:

Trophic Disturbances
a) skin status: of normal color;
b) atrophy of the injured hand and forearm muscles, compared to the normal arm: moderate (1-2 cm);
c) nail changes: within normal limits; and
d) secretory function: within normal limits.

Sensitivity Testing in the Patient in the Autonomous Zone of Innervation by the Nerve:

| No. | Kinds of Sensitivity | Brief Description |
|---|---|---|
| 1. | Pain | Present, including distal phalanges of all fingers |
| 2. | Temperature | Hot - distal phalanges of fingers 1 and 3, middle phalanges of fingers 4, 5 |
| | | Cold - distal phalanges of fingers 1, 3; distal phalanges of fingers 1, 2, 3, 4, 5 |
| 3. | Tactile | Fingers 1, 2, 3, 4, 5 - distal phalange |
| 4. | Discriminative | finger 1 - 5 mm |
| | | finger 2 - 5 mm |
| | | finger 3 - 10 mm |
| | | finger 4 - 5 mm |
| | | finger 5 - 10 mm |
| 5. | Sense of two-dimension space (Moberg pickup test) | Identifies large objects (a box of cigarettes, glue, tube for blood collection), as well as small objects (rubber, button, coin, clip) |
| 6. | Sense of pressure | Present |
| 7. | Sense of weight | present |

| Degree | Sensitivity recovery |
|---|---|
| S3+ | Recovery of surface pain and tactile sensitivity within the entire autonomous zone with complete hyperpathia disappearance, but with some recovery of two-point discrimination within the autonomous zone (from 12 to 15 mm) |

Motor Function Testing

| Degree | Motor function recovery |
|---|---|
| M4 | Movements with overcoming some resistance |

Figure 9:
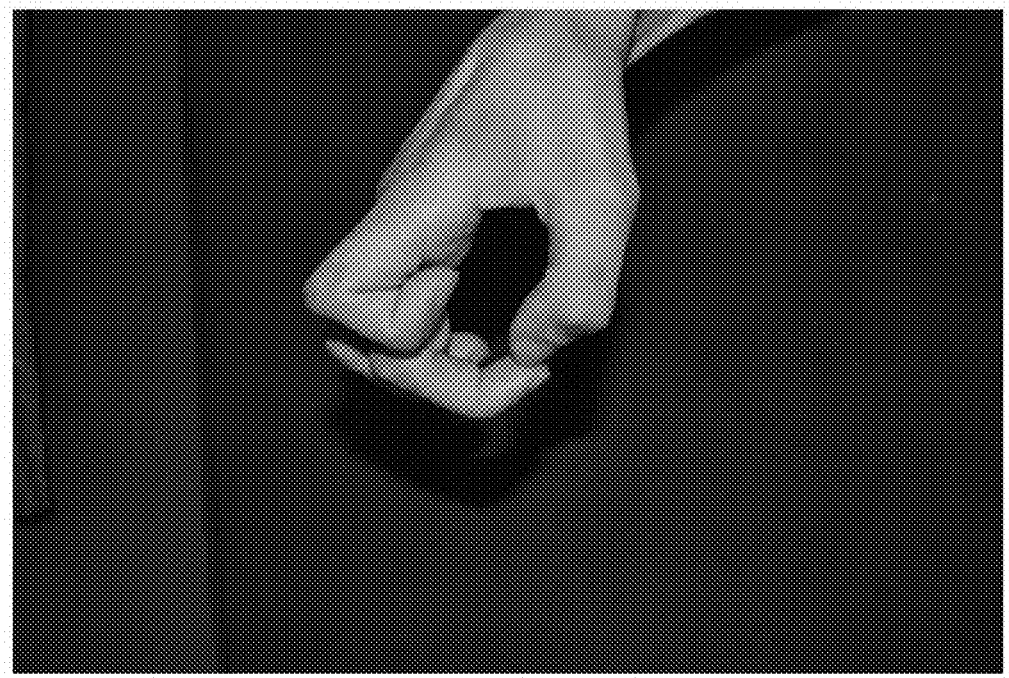
FIG. 9 shows a hook grasp (a purse handle). Figure demonstrates post-surgical improvement in patient's condition.
Figure 10:
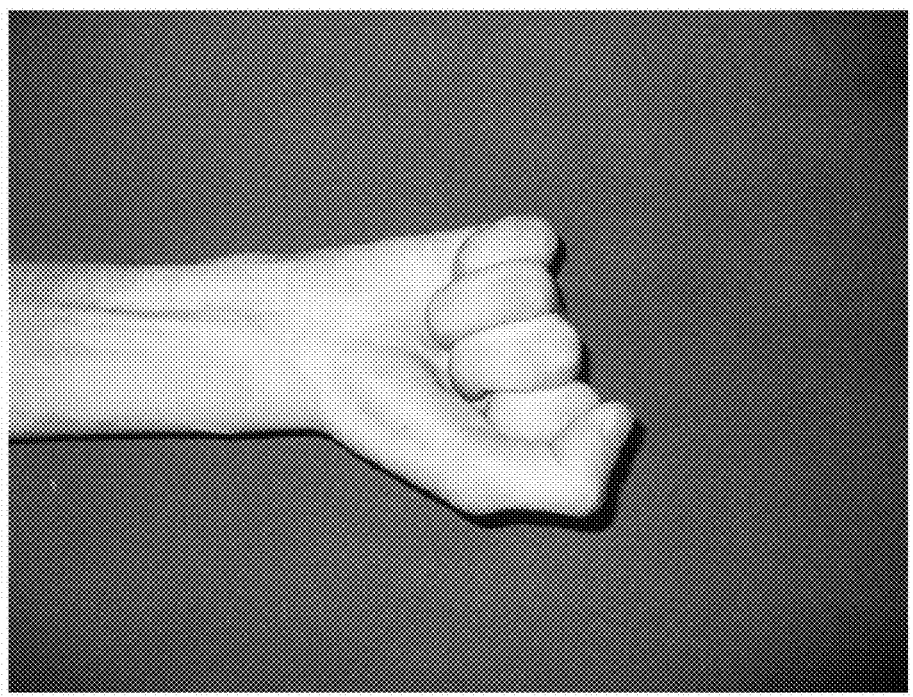
FIG. 10 shows a fist grasp. Figure demonstrates post-surgical improvement in patient's condition.
Figure 11:
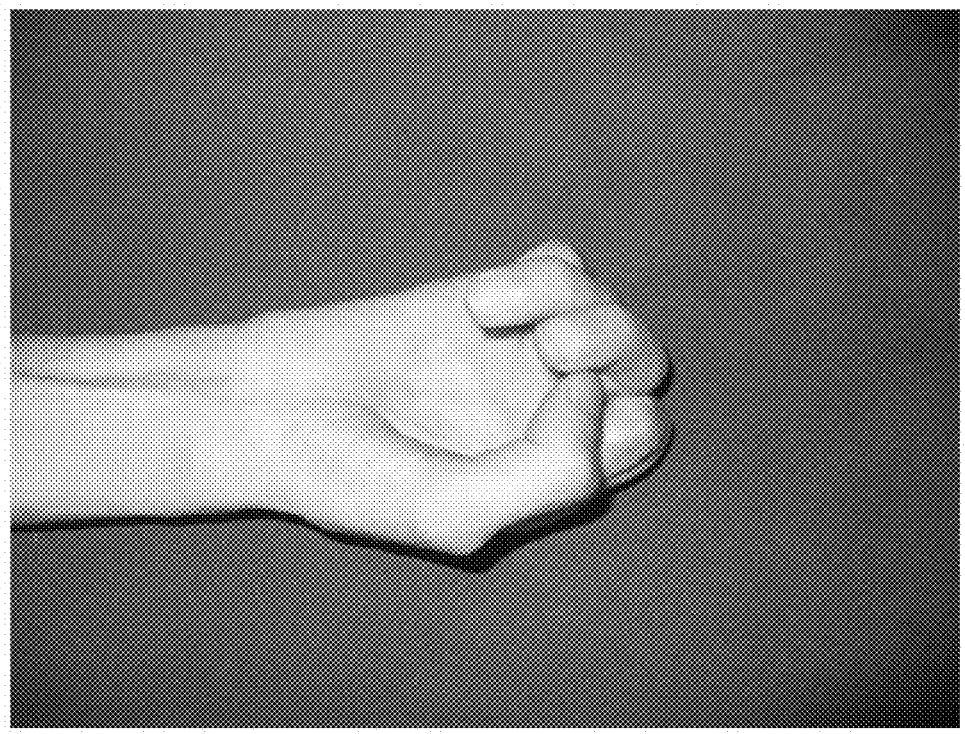
FIG. 11 shows tip prehension (finger Figure demonstrates post-surgical improvement in patient's condition.
Figure 12:
FIG. 12 shows tip prehension (finger Figure demonstrates post-surgical improvement in patient's condition.
Figure 13:
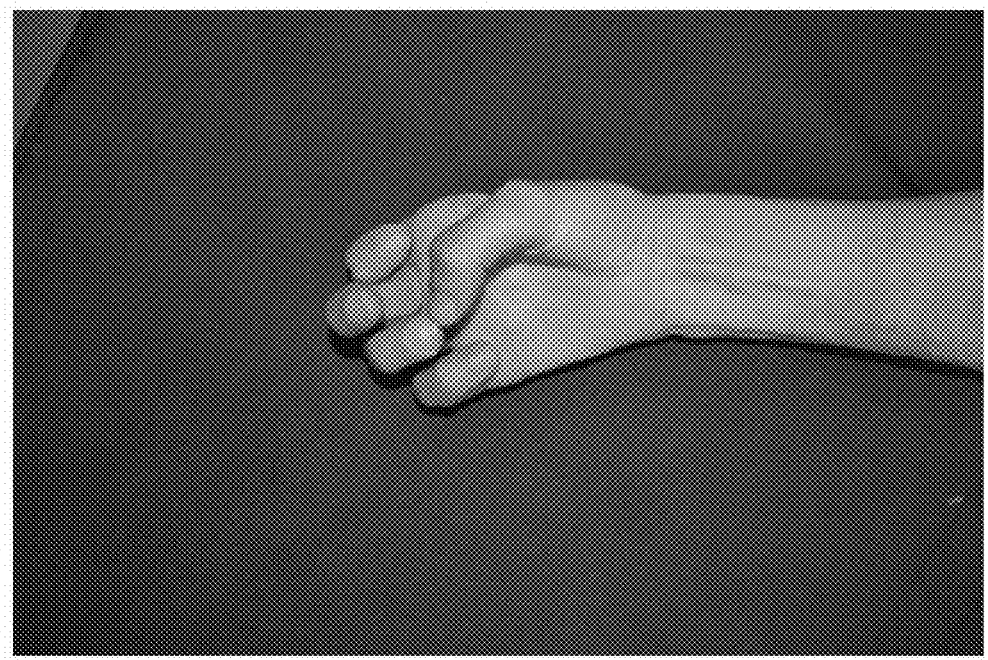
FIG. 13 shows tip prehension (finger I-IV). Figure demonstrates post-surgical improvement in patient's condition.

Hand Prehension Patterns:
1) spherical grasp—YES;
2) spherical grasp—YES;
3) hook grasp—YES (FIG. 9);
4) first grasp—YES (FIG. 10);
5) tip prehension: (FIG. 11-13)
   a) terminal opposition—YES;
   b) subterminal opposition—YES;
6) lateral prehension
   a) pinch grip—YES;
   6) scissor grip—YES.

Figure 14:
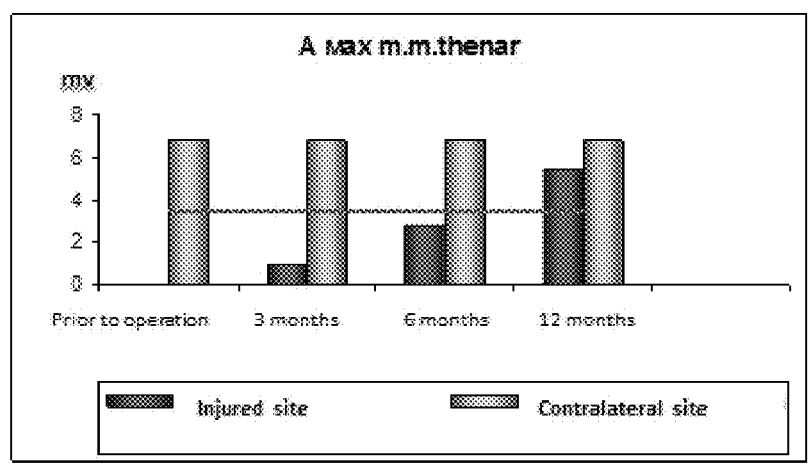
FIG. 14 shows a diagram of electromyography results for the thenar muscle group. Based on the electromyography results the thenar muscle response amplitude had increased over the year from 0 mV to 5 mV and almost achieved the value of the contralateral extremity.

These clinical results show that the extremity function was significantly improved one year after the intraneural administration of the gene-therapeutic construction containing a plasmid expressing VEFG and FGF2. The improved functional state of the extremity was manifested as the decreased severity of the trophic disturbances, as the development of various sensitivities within the area of innervation of the median and ulnar nerves, and as a significant improvement of the motor function. Based on the electromyography results the thenar muscle response amplitude had increased over the year from 0 mV to 5 mV and almost achieved the value of the contralateral extremity (FIGS. 14 and 15).

An animal model and clinical results show that a plasmid that expresses two growth factors, VEGF and FGF2, provides a more effective induction of the peripheral nerve regeneration that prior plasmid constructs.

The efficacy of using a gene therapeutic construction to improve results of surgical treatment of peripheral nerve injuries has been determined and demonstrated by the present inventors in the above described experiments and clinical observations. While not being bound to any particular mechanism, the inventors believe that the achieved clinical effects when using the plasmid pBud(Kan)-VEGF-FGF2 (SEQ ID NO: 1) were likely obtained due to the combination of these two growth factors. However, a full understanding of the influence of genetic constructs requires further studies.

Example 3. Codon Optimization (A) Codon optimization is based on the degeneracy of genetic code when the most commonly used synonymous codons of degenerate genetic code are used as optimal codons. The higher the frequency of occurrence of a codon used to encode an amino acid in the body the more rapidly it could be translated by ribosomes due to the high intracellular concentration of tRNA recognizing such codon. To optimize the codon composition of VEGF165 and FGF2 genes, the OptimumGene® algorithm was used, which takes into account various factors affecting gene expression levels such as codon shift, GC composition, CpG dinucleotide content, secondary mRNA structure, tandem repeats, restriction sites that can interfere with the cloning, premature polyadenylation sites, additional minor ribosome binding sites, etc. All these optimizations can result in increased target transgene transcription, mRNA stability and translation.

The nucleotide sequences of mRNA of VEGF165 gene (GeneBank #AF486837.1, 576 bp) and FGF2 gene (GeneBank #DD406196.1, 468 bp) were used as a template for the codon optimization. The codon usage bias in VEGF165 and FGF2 genes was changes by upgrading the codon adaptation index (CAI) from 0.81 to 0.87 and from 0.77 to 0.87, respectively. The GC content and unfavorable peaks have been optimized to prolong the half-life of mRNA. Stem-Loop structures that impact ribosomal binding and stability of mRNA were disturbed. In addition, the applied optimization process has screened and successfully modified the negative cis-acting sites as listed in the introduction. As a result of the codon optimization, the amino acid sequences of FGF2 and VEGF165 genes have not changed and were 155 and 191 amino acid residues, respectively.

De novo synthesis of codon-optimized VEGF165 and FGF2 cDNAs and subsequent subcloning into plasmid pBud(Kan)-coVEGF165-coFGF2 was performed by GenScript® (USA).

(B) A functional activity of the obtained genetic construct was confirmed by the analysis of transgenes expression in vitro.

A genetic modification (transfection) of HEK293T cells with plasmid pBud(Kan)-coVEGF165-coFGF2 was performed using TurboFect® transfection reagent (Thermo Fisher Scientific Inc., USA) according to the procedure recommended by the manufacturer. To evaluate efficiency of transfection plasmid vector pEGFP—N2 (BD Biosciences Clontech, Germany) expressing the green fluorescent protein GFP was used as a positive control.

To evaluate expression of VEGF165 and FGF2 in the transfected HEK293T cells immunofluorescence and xMap Luminex® (multiplex) assays were performed.

Immunofluorescence analysis of the expression of VEGF165 and FGF2 in the genetically modified HEK293T cells was performed 48 hours after transfection using a standard protocol using specific antibodies to VEGF (VEGF Antibody (A-20), #sc-152, Santa Cruz Biotechnology, Inc.) and FGF2 (FGF-2 Antibody (N-19), #sc-1390, Santa Cruz Biotechnology, Inc.). Results were analyzed by fluorescence microscopy on an inverted AxioOberver®.Z1 fluorescence microscope (Carl Zeiss, Germany) using AxyoVision Rel® software. 4.8. Immunofluorescence analysis of the HEK293T cells transfected with plasmid pBud (Kan)-coVEGF165-coFGF2 has revealed a positive reaction with specific antibodies to the vascular endothelial growth factor and the fibroblast growth factor (FIG. 16).

A level of secretion of VEGF and FGF2 by the genetically modified HEK293T cells was determined using Bio-Plex Pro™ Human Cytokine 27-plex Assay (BioRad) xMap Luminex® multiplex assay kit on the Luminex®200™ multiplex analyzer. The concentrations of FGF2 and VEGF in a conditioned medium of HEK293T cells transfected with plasmid pBud(Kan)-coVEGF165-coFGF2 were 825.21 pg/ml and 2145.8 pg/ml, respectively.

| Sample | Concentration of FGF2, pg/ml | Concentration of VEGF, pg/ml |
|---|---|---|
| pBud(Kan)-coVEGF165-coFGF2 | 825.21 | 2145.8 |
| pEGFP-N2 | 3.01 | 37.74 |
| Without plasmid | 3.05 | 24.75 |

Example 4. Clinical Evaluation of Regenerative Effects of pBud(Kan)-coVEGF165-coFGF2 (SEQ ID NO: 4)

Patient M., born in 1979, was admitted to the trauma center of the Republic Clinical Hospital of MoH of the Republic of Tatarstan in October 2014, with the diagnosis of sequelae of the median nerve injury in the middle third of the right upper arm.

From the patient's history, it was known that in December 2013, the patient had a knife cut of the middle third of the upper arm, with the median nerve damaged. Primary surgical treatment of the wound without suture of the median nerve was performed in the ambulance hospital in the patient's place of residence. In 10 months, the patient came to the clinic.

At the time of admission, there was a complete loss of function of the median nerve—lack of flexion of 1 and 2 fingers, lack of sensitivity. With palpation, there was a sharp soreness in the field of a trauma with characteristic "shooting" pain. Prior to surgery, on Oct. 20, 2014, the patient had an examination with the following results:

Trophic Disturbances:

a) skin status: normal color, decreased fingers' temperature, increased feeling of chillness;

b) atrophy of the hand and forearm muscles, as compared to the normal arm: more than 2 cm.

c) nail changes: hypoplastic; and d) secretory function (sweating): decreased.

Sensitivity Testing in the Patient in the Autonomous Zone of Innervation by the Nerve:

| No. | Kinds of Sensitivity | Brief Description |
|---|---|---|
| 1. | Pain | Absent |
| 2. | Temperature | Absent |
| 3. | Tactile | Absent |
| 4. | Discriminative | Absent |
| 5. | Sense of two-dimension space | Absent |
| 6. | Stereognosis | Absent |
| 7. | Sense of pressure | Absent |
| 8. | Sense of weight | Absent |

| Degree | Sensitivity recovery |
|---|---|
| S0 | Lack of sensitivity within the nerve autonomous zone |

Motor Function Testing

| Degree | Motor function recovery |
|---|---|
| M2 | Distinct contractions without movements in joints |

Hand prehension patterns: the hand is unable to perform any type of prehension.

Diagnosis: the injury of the median nerve in the middle third of the forearm sustained 10 months ago.

Figure 17:
FIG. 17 shows a 7 cm defect of a median nerve replaced by a sural nerve.

A surgery was performed on Oct. 21, 2014, including a 7 cm defect autonerve grafting by sural nerve (FIG. 17) of the median nerve with the intraneural administration of plasmid pBud(Kan)-coVEGF165-coFGF2 (SEQ ID NO: 4) containing the VEGF165 and FGF2 genes.

The surgery was conducted under the nerve block anaesthesia. Following triple treatment of the surgical field, an arcuate incision was made on the inner surface of the right upper arm. The median nerve was isolated with technical difficulties. There were neuroma signs observed and the nerve was involved in a scar-forming process and adhered to the surrounding tissue.

Figure 18:
FIGS. 18 and 19 show injection of the recombinant plasmid pBud (Kan)-coVEGF-coFGF2 into the grafted nerve into the suture zone and also proximally and distally over the length of 10 cm.
Figure 19:
Figure 20:
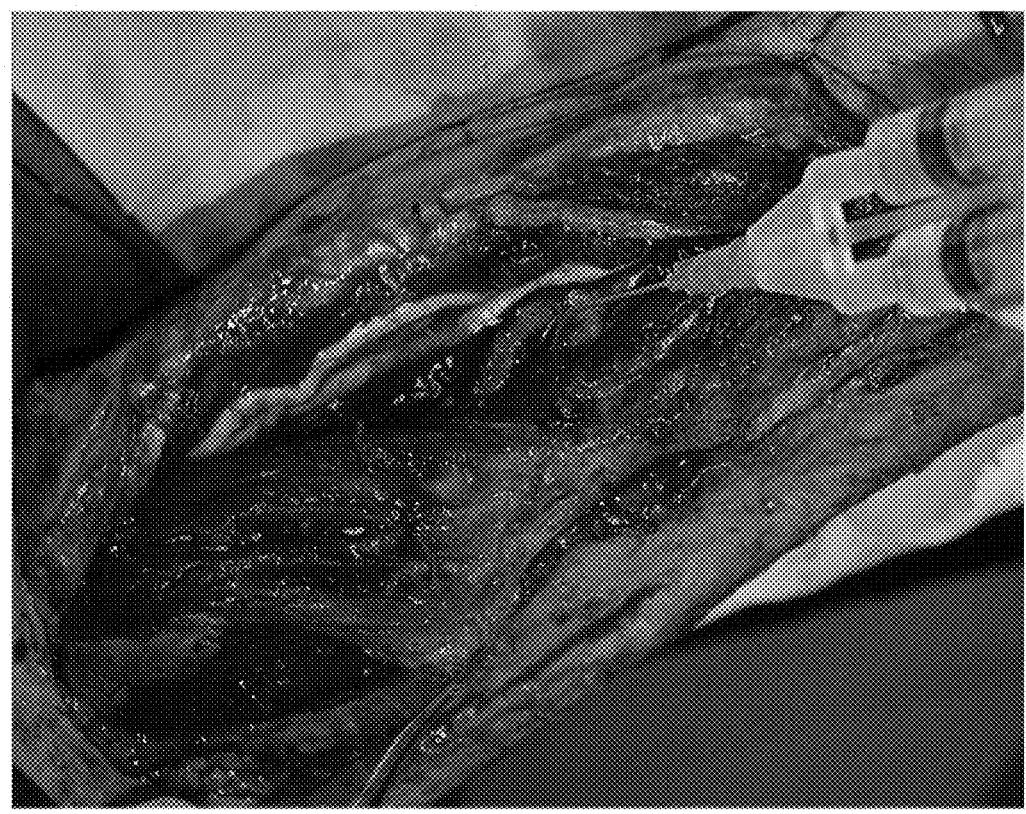
FIG. 20 shows application of fibrin glue to prevent leakage of the recombinant plasmid.

The plasmid pBud(Kan)-coVEGF165-coFGF2 was injected with an insulin needle, 250 pg in 2.5 ml of a physiologic saline solution. The injection was administered into the graft zones and also proximally and distally over the length of 10 cm (FIG. 18, 19). After that 2 ml of the two-component fibrin glue TISSUCOL® was applied to the isolated nerves (FIG. 20).

The post-surgical case included hemostasis, wound suturing, placement of a rubber tube drainage, and application of an antiseptic dressing and a plaster cast. A re-examination was performed one month after the surgery.

The results of the physical examination dated Nov. 21, 2014, are presented below:

Trophic Disturbances:
a) skin status: normal color;
b) atrophy of the injured hand and forearm muscles, compared to the normal arm: more than 2 cm;
c) nail changes: hypoplastic; and
d) secretory function (sweating): decreased.

Sensitivity Testing in the Patient in the Autonomous Zone of Innervation by the Nerve:

| No. | Kinds of Sensitivity | Brief Description |
|---|---|---|
| 1. | Pain | Absent |
| 2. | Temperature | Hot - absent<br>Cold - distal phalanges of fingers 1, 2 |
| 3. | Tactile | Fingers 1, 2 - distal phalange |
| 4. | Discriminative | Absent |
| 5. | Sense of two-dimension space (Moberg pickup test) | Absent |
| 6. | Sense of pressure | Present |
| 7. | Sense of weight | Present |

| Degree | Sensitivity recovery |
|---|---|
| S1 | Recovery of deep pain sensitivity within the nerve autonomous zone |

Motor Function Testing:

| Degree | Motor function recovery |
|---|---|
| M2 | Distinct contractions without movements in joints |

Hand prehension patterns: the hand is unable to perform any type of prehension.

A regular examination was performed in 6 months after the surgery. The results of the physical examination dated Apr. 20, 2015, are presented below:

Trophic Disturbances:
a) skin status: of normal color;
b) atrophy of the hand and forearm muscles, compared to the normal aim: moderate (1-2 cm) and severe (more than 2 cm);
c) nail changes: within normal limits; and
d) secretory function (sweating): normal.

Sensitivity Testing in the Patient in the Autonomous Zone of Innervation by the Nerve:

| No. | Kinds of Sensitivity | Brief Description |
|---|---|---|
| 1. | Pain | Present, including distal phalanges of all fingers |
| 2. | Temperature | Hot - distal phalanges of finger 1, middle phalanges of fingers 3, 4<br>Cold - distal phalanges of fingers 1, 3; distal phalanges of fingers 2, 4, 5 |
| 3. | Tactile | Fingers 1, 3 - distal phalange, middle phalange 2, 4, 5 |
| 4. | Discriminative | Finger 1 - 10 mm<br>Finger 2 - 30 mm<br>Finger 3 - 20 mm<br>Finger 4 - 30 mm<br>Finger 5 - 30 mm |
| 5. | Sense of two-dimension space (Moberg pickup test) | Identifies large objects (a box of cigarettes, glue, tube for blood collection), a pencil, glue tube |
| 6. | Sense of pressure | Present |
| 7. | Sense of weight | Present |

| Degree | Sensitivity recovery |
|---|---|
| S3 | Recovery of surface pain and tactile sensitivity within the entire autonomous zone with complete hyperpathia disappearance |

Motor Function Testing

| Degree | Motor function recovery |
|---|---|
| M3 | Mild movements in joints (useful recovery) |

Hand Prehension Patterns:
1) cylindrical grasp—YES;
2) spherical grasp—YES;
3) hook grasp (a bag handle)—YES;
4) first grasp—YES;
5) tip prehension
   a) terminal opposition—YES;
   b) subterminal opposition—NO;
6) lateral prehension
   a) pinch grip—NO;
   b) scissor grip—"cigarette"—NO.

A 1 year after the surgery, the patient had a regular examination. The results of the physical examination dated Oct. 26, 2015, are presented below:

Trophic Disturbances:
a) skin status: of normal color;
b) atrophy of the injured hand and forearm muscles, compared to the normal arm: moderate (1-2 cm) and severe (more than 2 cm);;
c) nail changes: within normal limits; and
d) secretory function: within normal limits.

Sensitivity Testing in the Patient in the Autonomous Zone of Innervation by the Nerve:

| No. | Kinds of Sensitivity | Brief Description |
| --- | --- | --- |
| 1. | Pain | Present, including distal phalanges of all fingers |
| 2. | Temperature | Hot-distal phalanges of fingers 1 and 3, middle phalanges of fingers 4, 5 Cold-distal phalanges of fingers 1, 3; distal phalanges of fingers 1, 2, 3, 4, 5 |
| 3. | Tactile | Fingers 1, 2, 3, 4, 5-distal phalange |
| 4. | Discriminative | Finger 1-5 mm Finger 2-5 mm Finger 3-10 mm Finger 4-5 mm Finger 5-10 mm |
| 5. | Sense of two-dimension space (Moberg pickup test) | Identifies large objects (a box of cigarettes, glue, tube for blood collection), as well as small objects (rubber, button, coin, dip) |
| 6. | Sense of pressure | Present |
| 7. | Sense of weight | present |

| Degree | Sensitivity recovery |
| --- | --- |
| S3+ | Recovery of surface pain and tactile sensitivity within the entire autonomous zone with complete hyperpathia disappearance, but with some recovery of two-point discrimination within the autonomous zone (from 12 to 15 mm) |

Motor Function Testing

| Degree | Motor function recovery |
| --- | --- |
| M4 | Movements with overcoming some resistance |

Figure 21:
FIG. 21 shows a cylindrical grip. Figure demonstrates post-surgical improvement in patient's condition.
Figure 22:
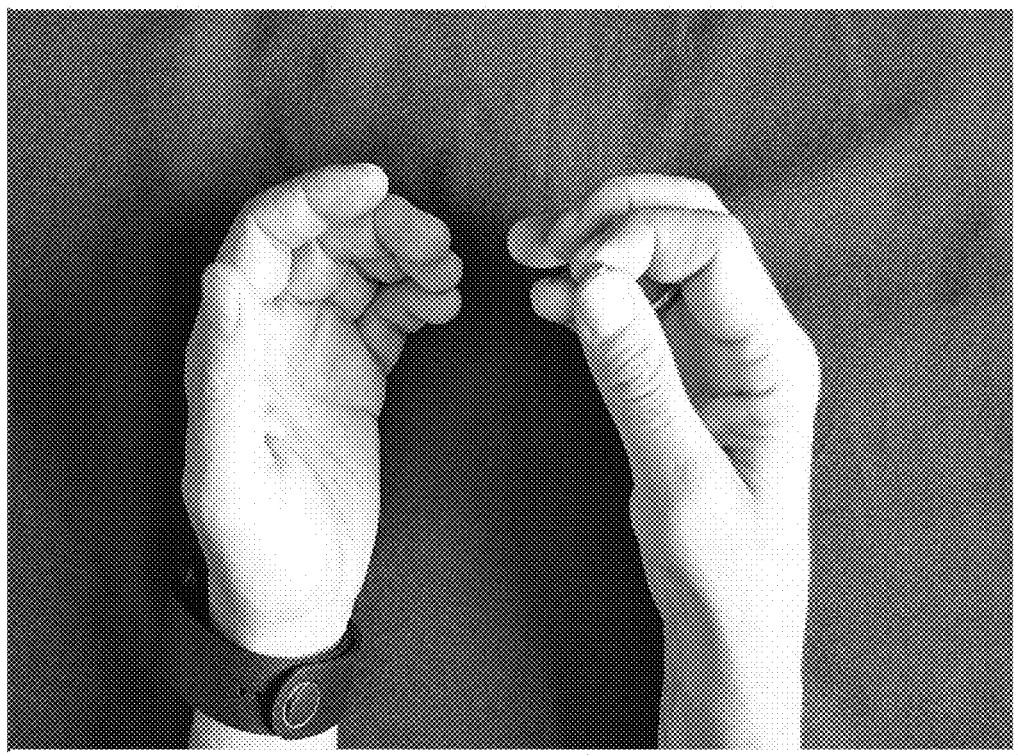
FIG. 22 shows a hook grasp (a purse handle). Figure demonstrates post-surgical improvement in patient's condition.
Figure 23:
FIG. 23 shows a fist grasp. Figure demonstrates post-surgical improvement in patient's condition.

Hand Prehension Patterns:
1) spherical grasp—YES (FIG. 21);
2) hook grasp—YES (FIG. 22);
3) first grasp—YES (FIG. 23);
4) tip prehension:
    a) terminal opposition—YES;
    b) subterminal opposition—YES;
5) lateral prehension
    a) pinch grip—YES;
6) scissor grip—YES.

These clinical results show that the extremity function was significantly improved one year after the intraneural administration of the gene-therapeutic construction containing a plasmid expressing VEFG165 and FGF2. The improved functional state of the extremity was manifested as the decreased severity of the trophic disturbances, as the development of various sensitivities within the area of innervation of the median nerve, and as a significant improvement of the motor function.

The in vitro experiments and clinical results show that a plasmid that expresses two growth factors, VEGF165 and FGF2, provides a more effective induction of the peripheral nerve regeneration that prior plasmid constructs.

The efficacy of using a gene therapeutic construction to improve results of surgical treatment of peripheral nerve injuries has been determined and demonstrated by the present inventors in the above described experiments and clinical observations. While not being bound to any particular mechanism, the inventors believe that the achieved clinical effects when using the plasmid pBud(Kan)-coVEGF165-coFGF2 (SEQ ID NO: 4) were likely obtained due to the combination of these two growth factors. However, a full understanding of the influence of genetic constructs requires further studies.

All publications, patent applications, patents, and other references mentioned herein are incorporated by reference herein in their entirety. Further, the materials, methods, and examples are illustrative only and are not intended to be limiting, unless otherwise specified.

Numerous modification and variations on the present invention are possible in light of the above teachings. It is therefore to be understood that within the scope of the appended claims, the invention may be practiced otherwise than as specifically described herein.

REFERENCES

1. Hudso, A. R. Timing of peripheral nerve repair: important local and neuropathological factors/A. R. Hudson/ Clinical Neurosurgery.-1977.-Vol. 24.-C. 391-405.
2. Deitch, E. A. Experience with 112 shotgun wounds of the extremities/E. A. Deitch, W. R. Grimes/J Trauma.-1984.-Vol. 24.-P. 600-603.
3. Analysis of upper and lower extremity peripheral nerve injuries in a population of patients with multiple injuries/C. A. Munro/J. Trauma.-1998.-Vol. 45.-P. 116-122.
4. Terenghi, G. Peripheral nerve regeneration and neurotrophic factors/G. Terenghi/J. Anat. 1999.-Vol. 194.-P.
5. Vascular endothelial growth factor has neurotrophic activity and stimulates axonal outgrowth, enhancing cell survival and Schwann cell proliferation in the peripheral nervous system/M. Sondell, M. Kanje. G. Lundborg/J Neurosci.-1999.-Vol. 19, No 14-P. 5731-40.
6. VEGF-A165b is an endogenous neuroprotective splice isoform of vascular endothelial growth factor A in vivo and in vitro/N. Beazley-Long [et al.]/J Pathol.-2013.-Vol. 183, No 3-P. 918-29.
7. Sondell, M. Vascular endothelial growth factor stimulates Schwann cell invasion and neovascularisation of acelular nerve grafts/M. Sondell, G. Lundborg, M. Kanje/Brain Res.-1999.-Vol. 846-P. 219-228.
8. Vascular, glial and neuronal effects of vascular endothelial growth factor in mesencephalic expiants cultures/ W. F. Silverman [et al.]/Neuroscience.-1999.—Vol. 90-P. 1529-1541.
9. Forstreuter, F. Vascular endothelial growth factor induces chemotaxis and proliferation of microglial cells/F. Forstreuter, R. Lucius, R. Mentlein/J. Neuroimmunol.-2002.-Vol. 132-P. 93-98.
10. Zhu, Y. Vascular endothelial growth factor promotes proliferation of cortical neuron precursors by regulating E2F expression/Y. Zhu [et al.]/J FASEB.-2003. Vol. 17-P. 186-193.
11. Induction of VEGF and its Flt-1 receptor after sciatic nerve crush injury/R. R. Islamov [et al.]/Neuroreport.-2004. Vol. 15, No 13-P. 2117-21.

12. Effects of vascular endothelial growth factor on nerve regeneration in acellular nerve grafts/J. M. Rovak [et al.]/J Reconstr Microsurg.-2004. Vol. 20, No 1-P. 53-58.
13. Vascular endothelial growth factor-loaded poly (lactic-co-glycolic acid) microspheres-induced lateral axonal sprouting into the vein graft bridging two healthy nerves: nerve graft préfabrication using controlled release system/H. Karagoz [et al.]/J Microsurgery.-2012. Vol. 32, No 8-P. 635-41.
14. Sondell, M. Vascular endothelial growth factor stimulates Schwann cell invasion and neovascularization of acellular nerve grafts/M. Sondell, G. Lundborg, M. Kanje/Brain Res.-1999. Vol. 846, No 2-P. 219-28.
15. The effect of vascular endothelial growth factor and brain-derived neurotrophic factor on cavernosal nerve regeneration in a nerve-crush rat model/P S. Hsieh [et al.]/BJU Int.-2003. Vol. 92, No 4-P. 470-5.
16. Grothe, C. Physiological function and putative therapeutic impact of the FGF-2 system in peripheral nerve regeneration-lessons from in vivo studies in mice and rats/K. Haastert, J. Jungnickel, C. Grothe/Brain Res Rev.-2006. Vol. 51-P. 293-299.
17. Furushol, M. Disruption of Fibroblast growth factor receptor signaling in non-myelinating Schwann cells causes sensory axonal neuropathy and impairment of thermal pain sensitivity/M. Furushol [et al.]/J Neurosci.-2009. Vol. 29, No 6-P. 1608-1614.
18. Tulio, V. R. Bone marrow-derived fibroblast growth factor-2 induces glial cell proliferation in the regenerating peripheral nervous system/V. R. Tulio [et al.]/ Molecular Neurodegeneration.-2012. Vol. 7, No 34-P. 1-17.
19. Sciatic nerve grafting and inoculation of FGF-2 promotes improvement of motor behavior and fiber regrowth in rats with spinal cord transaction/F. P. Guzen, [et al.]/Restorative Neurology and Neuroscience.-2012. Vol. 30-P. 265-275.
20. Zeng, W. Ionically cross-linked chitosan microspheres for controlled release of bioactive nerve growth factor/ W. Zeng [et al.]/Int J Pharm.-2011. Vol. 421-P. 283-290.
21. Enhancement of musculocutaneous nerve reinnervation after vascular endothelial growthfactor (VEGF) gene therapy/P. Haninec [et al.]/BMC Neuroscience.-2012. Vol. 13, No 57-P.
22. Effect of VEGF gene therapy and hyaluronic acid film sheath on peripheral nerve regeneration/F. Zor [et al.]/- 2014. Vol. 34, No 3-P. 209-16.
23. Favorable effect of local VEGF gene injection on axonal regeneration in the rat sciatic nerve/C. Fu [et al.]/J Huazhong University Scince Technology.-2007. Vol. 2-P. 186-9.
24. Double gene therapy with granulocyte colony-stimulating factor and vascular endothelial growth factor acts synergistically to improve nerve regeneration and functional outcome after sciatic nerve injury in mice/F. Pereira Lopes [et al.]/Neuroscience.—2013. Vol. 230-P. 184-97.
25. Pat. 2459630 RF, IPC A61K 48/00, A61P 25/28, C12N 15/79, C1. Stimulation Technique for Neuroregeneration with Genetic Constructions/Yu. A. Chelyshev; Federal State Educational Institution "Kazan Federal University".-No 2011116853/10; 27 Apr. 2011; published 27 Oct. 2009, Bull. No 30.-11 p. [in Russian]
26. Stimulation of post-traumatic regeneration of a rat sciatic nerve with a plasmid expressing the vascular endothelial growth factor and the basic fibroblast growth factor./R. F. Masgutov [et al]/Cell Technologies and Tissue Engineering.-2011.-6(3): 67-70. [in Russian].

The invention claimed is:

1. A method for treating peripheral nervous system damage or injury, or for regenerating peripheral nervous system tissue, the method comprising:
 administering to a subject in need thereof an effective amount of a vector that comprises polynucleotide sequences that encode a vascular endothelia growth factor (VEGF) and a fibroblast growth factor 2 (FGF2),
 wherein the administration is performed by injecting the vector (i) directly at a damage or injury site, (ii) at a site proximal to the injury or damage site, (iii) at a site distal to the injury or damage site, or a combination of (i)-(iii), of the median nerve in the middle third of the forearm of the subject,
 wherein the peripheral nervous system damage or injury is neurotmesis,
 wherein the vector comprises FGF2 encoding nucleotides at positions 699-1166 and VEGF165 encoding nucleotides at positions 3723-4298 of SEQ ID NO: 4, and
 wherein the vector expresses the VEGF and FGF2,
thereby treating peripheral nervous system damage or injury, or regenerating peripheral nervous system tissue.

2. The method of claim 1, wherein the vector is administered (i) directly at a damage or injury site.

3. The method of claim 1, wherein the vector is administered (ii) at a site proximal to the injury or damage site, (iii) at a site distal to the injury or damage site, or a combination of (ii)-(iii).

4. The method of claim 1, comprising administering the vector intra-, peri- and/or paraneurally.

5. The method of claim 1, comprising contacting the vector with a neuron, a Schwann cell, astrocyte, or microglia.

6. The method of claim 1, wherein the subject is human.

7. The method of claim 1, wherein the vector further comprises a polynucleotide sequence that encodes resistance to kanamycin.

8. The method of claim 1, wherein the vector comprises resistance to kanamycin nucleotides at positions 1469-2511 of SEQ ID NO: 4.

9. The method of claim 1, wherein the vector is pBud (Kan)-coVEGF165-coFGF2 having the nucleotide sequence of SEQ ID NO: 4.

* * * * *